United States Patent [19]

Vardanega et al.

[11] Patent Number: 5,641,457
[45] Date of Patent: Jun. 24, 1997

[54] STERILE FLOW CYTOMETER AND SORTER WITH MECHANICAL ISOLATION BETWEEN FLOW CHAMBER AND STERILE ENCLOSURE

[75] Inventors: Michael H. Vardanega, Livermore; Raymond Swan, Fremont; John Joubran, Santa Clara; David J. Medeiros, San Francisco; Edie Tichenor, Portola Valley; Hugh Lewis, San Francisco, all of Calif.

[73] Assignee: Systemix, Palo Alto, Calif.

[21] Appl. No.: 428,693

[22] Filed: Apr. 25, 1995

[51] Int. Cl.$^6$ .................................................. G01N 27/00
[52] U.S. Cl. ................................. 422/82.01; 422/82.05; 422/104; 356/72; 356/73; 356/244; 250/461.2
[58] Field of Search ......................... 422/81, 82.01, 422/82.02, 82.05, 104; 356/72, 73, 244; 250/461.2; 209/2, 3.1

[56] References Cited

U.S. PATENT DOCUMENTS

| | | | |
|---|---|---|---|
| 3,560,754 | 2/1971 | Kamentsky | 250/218 |
| 4,111,753 | 9/1978 | Folsom et al. | 195/126 |
| 4,230,031 | 10/1980 | Pedroso et al. | 98/115 LH |
| 4,304,224 | 12/1981 | Fortney | 128/1 R |
| 5,083,558 | 1/1992 | Thomas et al. | 128/202.12 |
| 5,150,313 | 9/1992 | Van Den Engh et al. | 364/569 |
| 5,200,616 | 4/1993 | Kokawa et al. | 250/306 |
| 5,464,581 | 11/1995 | Vanden Engh | 422/82.01 |

FOREIGN PATENT DOCUMENTS 9405775  3/1994  WIPO.

OTHER PUBLICATIONS

Dean, P.N. "Commercial Instruments, " in: Flow Cytometry and Sorting, Second Edition (Wiley-Liss Inc., 1990), pp. 171-186 1990.

Lindmo, T. et al. "Flow Sorters for Biological Cells," in: Flow Cytometry and Sorting, Second Edition (Wiley-Liss, Inc. 1990) pp. 145-169 1990.

(List continued on next page.)

*Primary Examiner*—Jeffrey Snay
*Attorney, Agent, or Firm*—Blakely, Sokoloff, Taylor & Zafman

[57] ABSTRACT

An apparatus and process for measuring particles that prevents the particles from being contaminated during the measuring and optional sorting process wherein a flow chamber or region is mechanically isolated from a sterile enclosure which surrounds the flow chamber. The present invention in one embodiment provides an apparatus comprising of a droplet generator, a charging system, a deflecting system, a sterilization system, a light source, a detector, a cooling system and a vacuum system. The droplet generator and the charging system and the flow chamber associated with the droplet generator operate within an illumination frame where the particles (e.g. biological cells) are actually measured. In order to prevent the biological cells from being contaminated, the illumination frame is located within an isolation chamber which provides an environment that can be sterilized before and after the actual measuring and sorting of the cells, but the illumination frame is mechanically isolated from the isolation chamber. The sterilization system, located outside the isolation chamber sterilizes the isolation chamber before cells are measured and sorted within the isolation chamber, and furthermore, ensures that the isolation chamber is maintained at a pressure above (or alternatively, below) atmospheric pressure during the measuring and sorting of the biological cells. The illumination frame, the light source and the detector are supported by a table to enable the light beam(s) from the light source to intersect the biological cells flowing through the illumination frame, thereby emitting flashes of light (or otherwise effecting the light beam) which are detected by the detector.

18 Claims, 23 Drawing Sheets

OTHER PUBLICATIONS

Steen, H.B. "Characteristics of Flow Cytometers," in: Flow Cytometry and Sorting, Second Edition (Wiley–Liss, Inc. 1990) pp. 11–25 1990.

Melamed, M.R. et al. "An Historical Review of the Development of Flow Cytometers and Sortes," in: Flow Cytometry and Sorting, Second Edition (Wiley–Liss, Inc. 1990) pp. 1–9 1990.

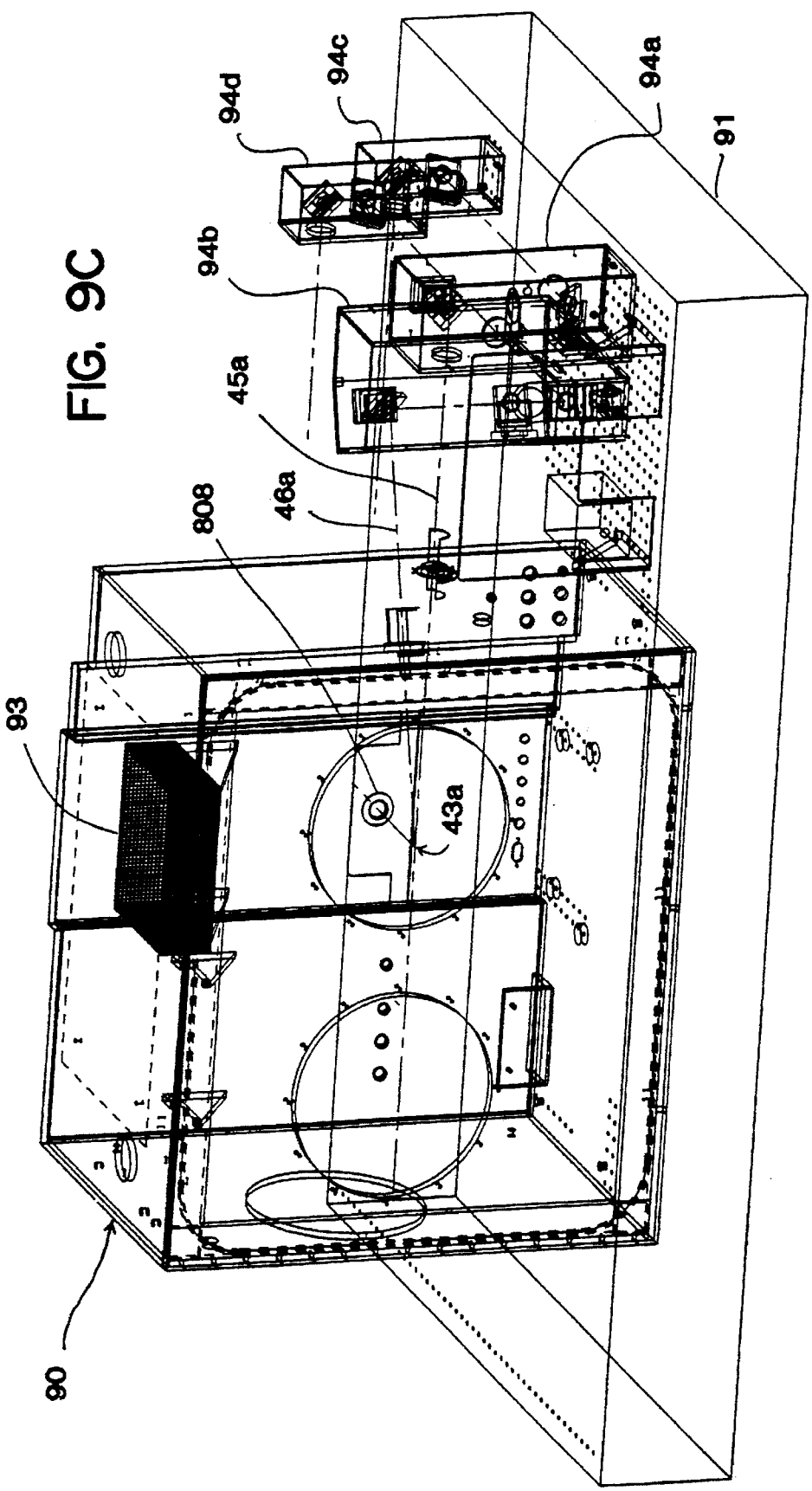

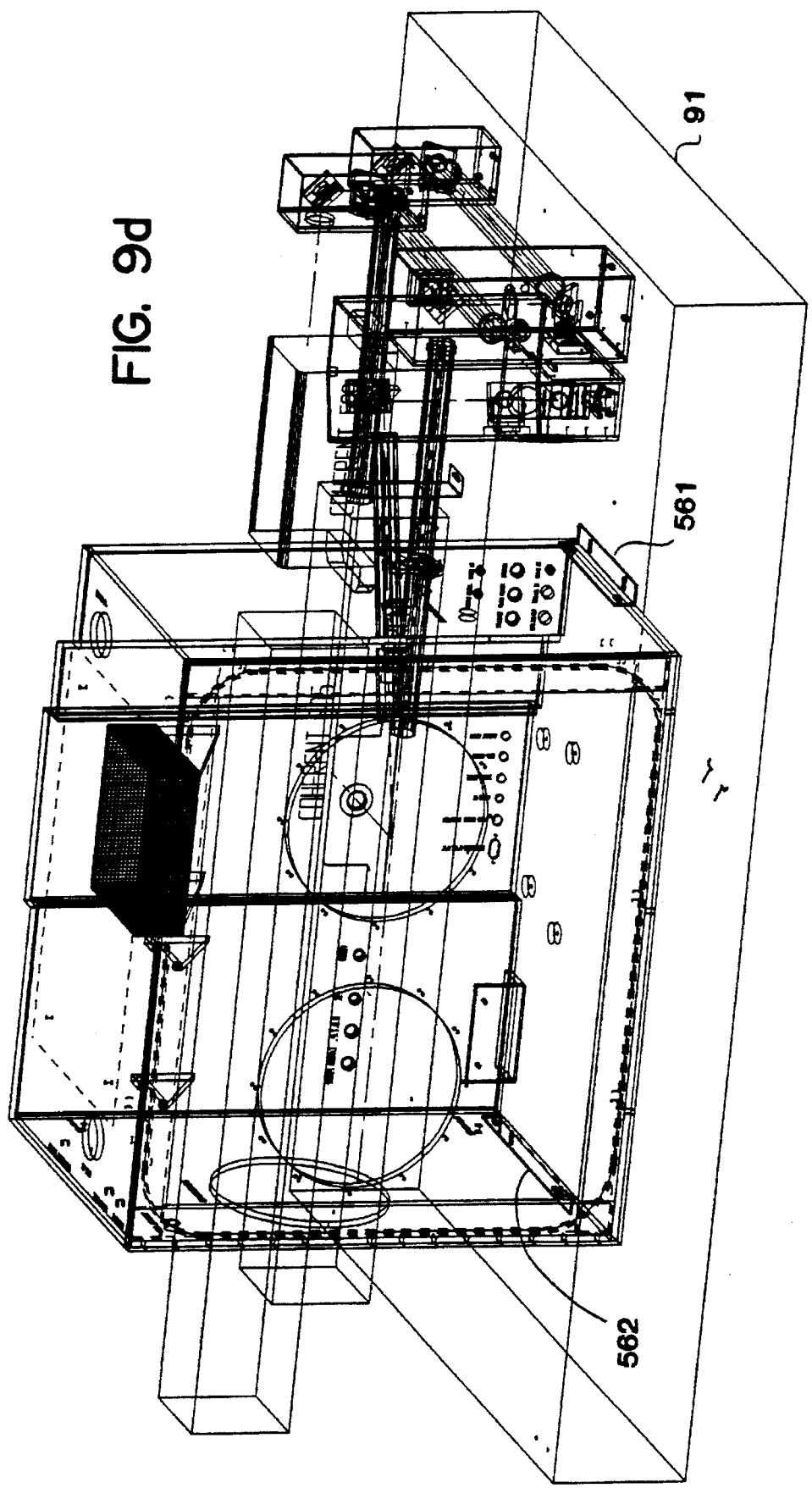

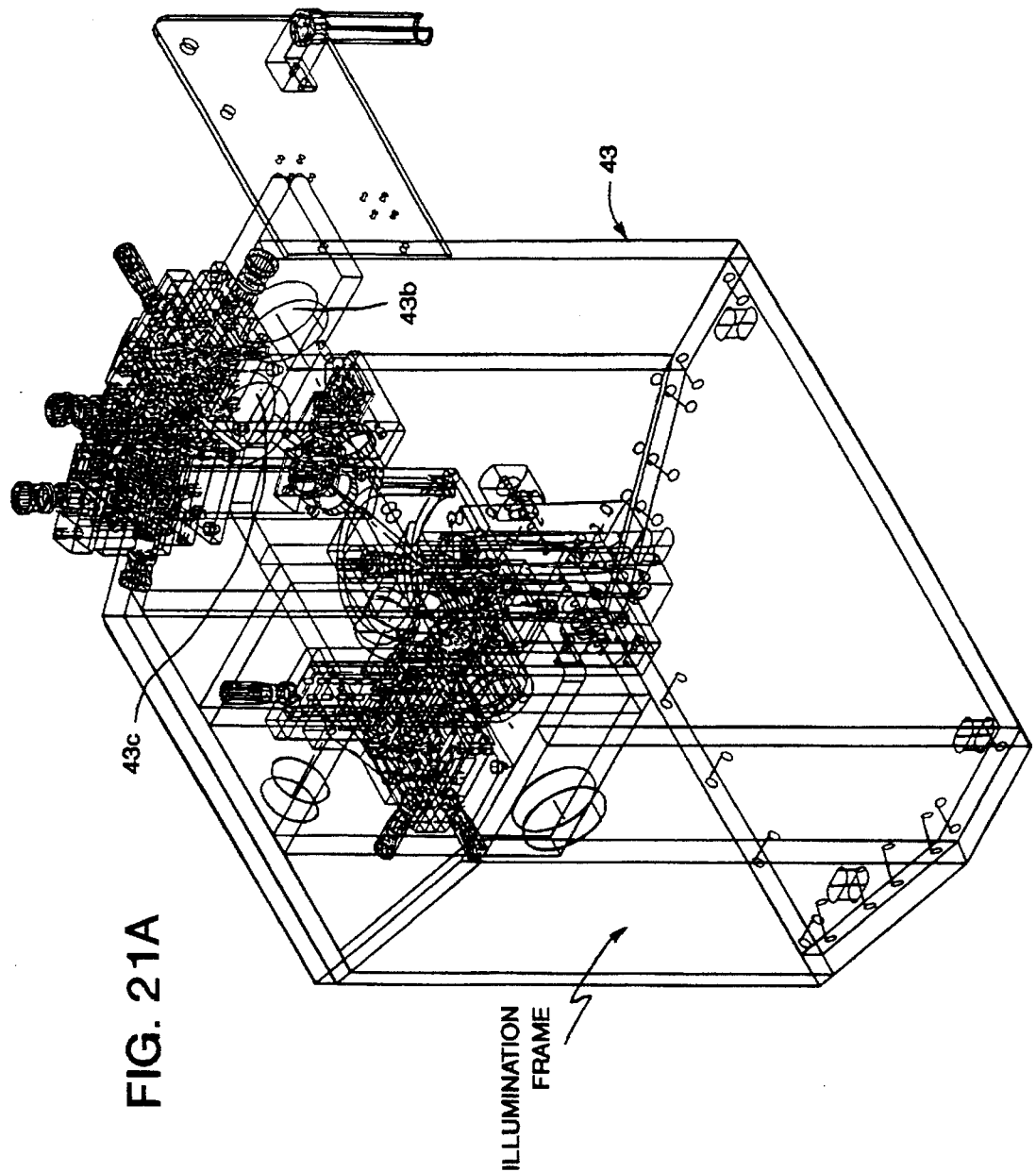

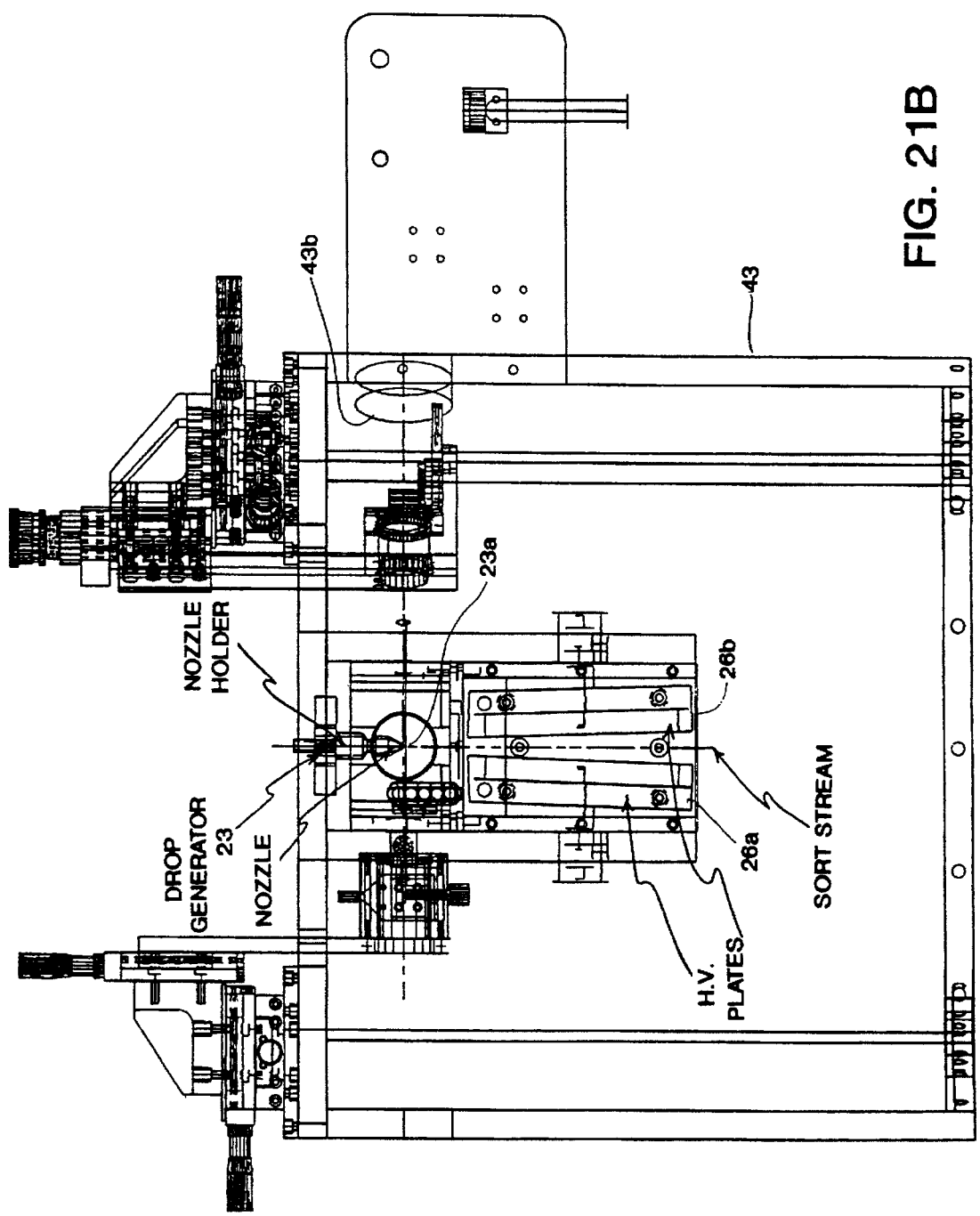

STERILE FLOW CYTOMETER AND SORTER WITH MECHANICAL ISOLATION BETWEEN FLOW CHAMBER AND STERILE ENCLOSURE

BACKGROUND

This invention relates to a method and apparatus for measuring certain parameters of particles and then optionally sorting the particles according to the values of the parameters measured, especially biological cells or portions of biological cells that are measured and sorted.

A cell sorter is an instrument that physically separates cells according to certain parameters. Many cell sorters use techniques to distinguish subpopulations of cells by employing a unique blend of modern technologies such as fluidics, electric fields, lasers, optics, analog and digital electronics, and computers and software. These techniques are often referred to as flow cytometry.

In a typical, conventional use of flow cytometry, selected cells are labeled with fluorescent molecules that bind specifically to the constituent(s) (e.g. using a fluorescently-labelled antibody to a particular surface antigen) to be measured. Certain, desired cells (a subpopulation of cells) are fluorescently labeled while other cells in the sample of cells are not fluorescently labeled, such that the fluorescently labeled cells may be selectively identified from a heterogeneous cell population. These fluorescently labeled cells are contained within the sample of cells that will be measured and sorted. Referring to FIG. 2, the sample of cells in a stream of a saline solution and a cell-free sheath fluid are supplied to a droplet generator 23 by cell sample inlet 23c and sheath fluid inlet 23d respectively. The sheath fluid confines, by hydrodynamic focusing, the sample of cells to a central core of the laminar flow that is leaving the droplet generator at orifice 23a. Before droplet generator 23 actually forms droplets, the combined stream of sheath fluid and labeled cells flows through a measuring region in an illumination frame which holds the droplet generator.

Inside the measuring region, the cells in the sample of cells pass, typically one by one, through a beam of excitation light from a light source 21 (e.g. a laser or arc lamp), such that each fluorescently labeled cell produces a short flash of fluorescence when passing through the light beam, the intensity of which is proportional to amount of the fluorescent label on the cell. These flashes of fluorescence are collected by a fluorescence collection lens 24b, which focuses the light on a sensitive fluorescence detector 24a. Detector 24a transforms the flashes of light into electrical pulses, which are measured and recorded by electronics 24c and optionally a computer 24d. Each cell also causes scattering of the excitation light at least in the case where the light source is a laser. The pattern of this scattering is a function of the size, shape and structure of the cell. The resulting flash of scattered light is recorded by a light scattering detector 24f and electronics 24e. Multiple fluorescence detectors may be used to detect several different fluorescent conjugates bound to the same or different cells in order to further distinguish different cell types in a heterogeneous mixture. Thus, multiple parameters including fluorescence at different wavelengths, as well as size and shape or structure, are recorded for each individual cell in the sample of cells.

Once these measurements are made, the cell sorter has the ability to selectively remove certain cells from the jet of sheath fluid. Just before the droplet-separation point, which occurs shortly after the cells leave the nozzle having the orifice 23a which is typically at the bottom of droplet generator 23, the droplets containing selected cells become selectively charged by a charging pulse 25a which is applied to the conductive fluid carrying the sample cells into the droplet generator 23. The charging pulse 25a is produced by a charging system control logic 24g which is coupled to receive signals from electronics 24c and electronics 24e; these signals indicate whether the cell, which was measured in the measuring region of the jet intersected by the beam of light from the light source 21, is a selected cell which is to be charged. The charging system control logic 24g analyzes these signals and determines whether the cell is to become a selected cell and, if so, applies the charging pulse to the conductive fluid carrying the cells just before the droplet carrying the cell breaks off of the jet of fluid. The jet leaving the orifice 23a is a substantially continuous stream of conductive fluid which applies the charging pulse, typically applied near the top of the droplet generator, to reach the droplet which is about to fall off of the jet below the orifice. The droplet carrying the selected cell separates as a charged droplet from the jet and falls, under the force of gravity, through a constant electric field produced by the deflecting system 26. If the cell that was measured is not a selected cell, then charging system control logic 24g will not apply the charging pulse, and the droplet containing this cell will separate from the jet as an uncharged droplet and will fall through the electric field largely unaffected by this field. Typically, one droplet will contain only one cell so that the selective charging of a droplet will select only one cell. The droplets are formed in the conventional manner by the ultrasonic vibrations of the ultrasonic transducer 23b which is coupled to droplet generator 23 which is supported by the illumination frame.

The charged and uncharged droplets then pass through a constant electrostatic deflection system 26 typically having a negative and a positive deflecting plate. Deflecting system 26 alters the trajectory in which the charged droplets are traveling such that the charged droplets are physically separated from the uncharged droplets according to the value of the parameters measured by the electronics. After passing through deflecting system 26, the droplets are collected in a cell collector 27 which may have several different collection receptacles. For more general background information refer to Flow Cytometry and Sorting, Second Edition by Myron R. Melamed, Tore Lindmo, Mortimer Mendelsohn, published by Wiley-Liss NY, NY, 1990. Also see, for example, U.S. Pat. No. 5,150,313, and U.S. Pat. No. 3,560,754.

Cell sorters have the ability to measure several parameters of each individual cell to determine the size, structure, and the precise contents of various cellular constituents. Today, flow cytometers can measure cells and other particles all the way down to submicroscopic sizes, that is, to approximately 0.1 μm and have sensitivities sufficient to detect $10^{-18}$ grams of a specific substance per cell. The ability to make multiple measurements on each cell, together with the resolution and sensitivity attainable with such measurements in cell sorters, makes possible the isolation of cell subpopulations having a purity and specificity of function that can be obtained in no other way.

Cell sorters are used in various fields of biology and medicine, including cell-cycle studies in relation to effects of drugs and radiation, immunology, ploidy determination in cancers, and studies of cellular parameters. For example, a flow cytometer can readily distinguish between different phases of the cell cycle in asynchronously growing cell cultures or can discriminate between different subsets of lymphocytes in immunology.

Although technology has led the way for a new generation of cell sorters that are simpler to operate and maintain, and significantly less expensive both to purchase and to operate, the inability to measure and sort cells in a sterile environment significantly limits the types of applications for the cell sorter. While small enclosures around the nozzle, droplet generator, electrostatic deflection plates, and collection receptacles have been suggested and used to protect users of the cell sorter from aerosols (generated around the nozzle) containing hazardous materials, these enclosures have not maintained the sterility of the cell stream before, during and after the sorting of the cells. The development of a cell sorter which is reliable, easy-to-use, and economical, and capable of operating in a sterile manner is necessary to achieve more widespread acceptance of the cell sorter, in both the clinical and research uses. Moreover, the enclosed environment protects the user of the flow cytometer from unsafe contaminants or cells which may be in the sample being measured and optionally sorted.

SUMMARY OF THE INVENTION

The unique process and apparatus provided by the present invention measures and sorts biological cells in an environment that prevents contamination of cells during the measuring and sorting of the cells. In one embodiment, the apparatus is a flow cytometer which measures, but does not sort, cells. In other words, the present invention produces sorted cells that are in a sterile environment. The ability to measure and sort cells in a sterile environment is crucial when handling biological cells that are intended to be used for further cultivation or other processes requiring sterility. Furthermore, the sterile environment provides greater protection for the user of the cell cytometer, such that the user is protected from any contaminants in the enclosed environment.

Therefore, it is desirable to provide an enclosed environment which can be sterilized and furthermore, maintain its sterility during the actual measuring and sorting of the cells. Although the present invention includes several subsystems, it is essential to have only certain subsystems located within the enclosed environment, but when these subsystems work in conjunction with those subsystems located outside the enclosed environment, the sterility of the enclosed environment must not be destroyed.

It is further desirable to provide an enclosed environment that is functional. In other words, in addition to encompassing the subsystems that must be kept sterile, the enclosed environment must provide an environment in which the user, located outside the sterile environment can properly operate the cell sorter within the enclosed environment. The enclosed environment should include adequate work space for the operator, the proper equipment and tools as well as a storage place for them when not in use, a transfer port for transferring items in and out of the enclosed environment without breaking the sterility of the isolation chamber, adequate safety mechanisms to prevent the operator from being injured, and an interface for the operator to conveniently and comfortably work inside the sterile environment while located outside the enclosed environment.

It is also desirable to provide a method for sterilizing the enclosed environment before measuring and sorting the cells, and for maintaining a sterile air pressure within the enclosed environment during the measuring and/or sorting of the cells. Sterilization may be repeated at the end of measuring and/or sorting in order to decontaminate the enclosure when measuring and/or sorting cells or samples which may be infected (e.g. HIV infected blood). This sterilization after measuring and/or sorting protects the user of the cell sorter form unhealthy contaminants.

The present invention is a system that includes several different subsystems integrating many different technologies. Although the biological cells are measured and physically separated in a sterile environment enclosed within an isolation chamber, many of the subsystems may be located outside of the isolation chamber. For example, the subsystems which are involved in taking the actual measurements, or in controlling the conditions of the sterile environment, or in controlling the operation of subsystems within the sterile environment, may all be located outside the isolation chamber. These external subsystems are connected to the subsystems located inside the isolation chamber by various tubes and pipes which pass through openings in the isolation chamber. These connections through the walls of the isolation chamber are sealed connections thereby ensuring that the isolation chamber is leakproof during the actual measuring and sorting of the cells.

The sterilization system is a subsystem in the present invention, which sterilizes the isolation chamber before cells are measured and sorted within the isolation chamber. Furthermore, the sterilization system ensures that, in a typical embodiment, during the measuring and sorting of the cells, the isolation chamber is maintained at a pressure above atmospheric pressure which is used to maintain the sterility of the isolation chamber. The sterilization system, typically located outside the isolation chamber, injects and withdraws the sterilant and air into and out of the isolation chamber through openings in the walls of the isolation chamber. In an alternative embodiment, the sterilization system may bathe the isolation chamber with short wavelength ultraviolet radiation in order to sterilize the isolation chamber; in this embodiment, the ultraviolet light sources are typically coupled to the isolation chamber and are inside the chamber.

The light source is another subsystem typically located outside the isolation chamber. The light source provides a primary and, if necessary, secondary laser beam (or beam of light from an arc lamp in an alternative embodiment) which focuses on the cells flowing through the measuring region within the illumination frame of the present invention. Once the laser beams intersect a cell, that cell will emit a fluorescent light if fluorescently labeled. Cellular constituents that have properties to be measured are typically labeled with some type of fluorescent molecule. Furthermore, the light system has, in one embodiment, two laser safety pipes within the isolation chamber and two laser safety pipes outside the chamber. The laser safety pipes provide a protective device in which the primary and secondary laser beams travel.

The detector system, including optics, detectors, and electronics, is also a subsystem of the present invention. The detector system is typically located outside the isolation chamber, except for its objective lens which extends inside the isolation chamber for collecting the flashes of fluorescent light emitted by the cells flowing in the measuring region. Once the light emitted by the cells are collected by the optics and focused upon the light detectors, the flashes of light are transformed into electrical pulses, which are measured and recorded by some electronics and, in one embodiment, a computer.

The illumination frame, which is located inside the isolation chamber, includes several other subsystems, namely the droplet generator, and the charging system. Included in the droplet generator is an ultrasonic transducer (e.g. a piezoelectric crystal) for vibrating the nozzle, a nozzle holder for injecting the sample biological cells into a jet of sheath fluid, and a nozzle cap for providing an orifice for the sort stream. The illumination frame typically provides mechanical support for the droplet generator and the charging system. This mechanical support holds these elements such that the portion of the jet carrying the cells in the measuring region of the jet is accurately aligned with the light source and detectors to ensure the intersection of the typically small laminar flow of cells (approximately less than 30 μm in cross-sectional diameter) with the beam of light from the light source (which beam itself is typically small). The illumination frame may also provide support for the deflecting system and the cell collector, and thus the deflecting system and the cell collector may be considered part of the illumination frame.

Immediately after leaving the droplet generator, the cells flowing in a substantially single file in a stream of sheath fluid through a measuring region, intersect the laser beam(s) which cause the biological cells labeled with fluorescent molecules to emit flashes of fluorescence. Almost every cell flowing in the stream of sheath fluid through the measuring region is isolated into a separate droplet shortly after leaving the nozzle. The measuring region is sometimes referred to as a flow chamber.

After the cells leave the nozzle in an unbroken column of fluid, and before the droplets are formed, the charging system selectively charges each droplet just as it is breaking off of the unbroken column of fluid such that when the droplets are formed, each droplet is independently and selectively charged (or not charged). In some embodiments a small group (e.g. 2) of droplets may be collectively charged or uncharged. In other words, after each cell is measured while flowing through the measuring region, the measurements made by the detector system determine whether a particular droplet containing a particular cell should be charged. If the measurements require that particular droplet to be charged, an electrical pulse, generated by the charging system control logic, is applied to the unbroken column of fluid such that the entire column of fluid is temporarily charged. When a droplet (containing that particular cell) is generated, that droplet becomes independently charged and the unbroken column of fluid returns to its neutral (or grounded) state until the detector system determines to charge another droplet containing another cell. Thus, droplets generated from the nozzle of the droplet generator are independently and selectively charged, depending on measurements made by the detector system. Note that the electronics in the detector system generally include the control logic for determining the amount of charge applied to each droplet.

After selectively and independently charging each droplet, each droplet passes a deflecting system having two charged deflection plates for establishing a constant transverse electrostatic deflection field. By deflecting each droplet into a specific collection receptacle within the cell collector subsystem, the present invention physically separates cells based on the values of the properties measured.

Also usually located within the isolation chamber, but typically not a part of the illumination frame, is the cell station. The cell station provides the droplet generator with biological cells that are chilled and stirred. The cell station inputs, passing through the walls of the isolation chamber, are sealed to the isolation chamber in order to prevent any leakage into the isolation chamber.

The vacuum system, also a subsystem of the present invention is located outside the isolation chamber, except for vacuum tubing which is inserted into sealed openings in the isolation chamber. The vacuum tubing is coupled to both the nozzle holder and the cell collector. The vacuum system removes debris that may clog up the nozzle and the contents of specific collection receptacles that contain unwanted cells or waste. The vacuum system discards the waste into waste containers located outside the isolation chamber.

In order the keep the cells alive during the measuring and sorting of the cells, in the typical embodiment the cells are maintained at a cool temperature by placing the cell station and cell collector in cooling blocks. A cooling line, inserted through a sealed opening in the isolation chamber, runs through each cooling block before passing the cooling line out of the isolation chamber through another opening in the isolation chamber. Within the cooling line flows a cooling mixture generated by a chiller.

The illumination frame, the detector(s), and the light source(s) are positioned on a table or other surface/structure such that the light beam path and the detecting optical path intersect in the measuring region of the jet where the cells pass in a single file. The isolation chamber is typically attached to the table or other surface/structure. The illumination frame, located within the isolation chamber, is also attached to the table such that small mechanical flexing of the isolation chamber (e.g. when the operator inserts his or her hands into the glove ports of the isolation chamber or moves such hands while in the glove ports) does not alter the position of illumination frame relative to the optics (source and detecting optics) on the laser table. Note that small movements in the isolation chamber (e.g. caused by the operator's hand movements) may prevent the laser beam path and/or detector optical path from intersecting the jet of cells flowing through the measuring region. According to the present invention the illumination frame, which supports the droplet generator typically also supports a portion of the light source optics and detector optics, is mechanically isolated from the isolation chamber. This mechanical isolation prevents small movements of the isolation chamber from affecting the alignment of the measuring region of the jet of cells (which might be as small as about 20 μm in cross-sectional diameter) relative to the light source's beam and detecting optics. This mechanical isolation allows use of the isolation chamber's glove ports while cell sorting is occurring.

A sterile cell sorter prevents cells from being contaminated and also maintains their viability, thereby allowing the sorted cells to be used for further processes such as genetic modification of the isolated cells, saving the isolated cells in a frozen state, or culturing the isolated cells in conventional tissue culture media, administering the isolated cells to a patient, or a combination of these or other processes. An example of such a combination might involve removing a sample of blood from a patient, labeling certain cells (e.g. pluripotent hematopoietic stem cells) with fluorescently labeled antibodies and isolating these cells using the sterile cell sorter by observing and measuring the emitted excitation wavelengths from these fluorescently labeled antibodies, culturing these isolated certain cells and genetically modifying them (e.g. using recombinant DNA technology) to provide genetically modified cells, and culturing these cells in a tissue culture media and injecting them back into the patient to provide a cure or remedy for a disease. The cell sorter of the present invention may also be used to separate a subpopulation of cells which are non-aberrant from other cells which are aberrant (e.g. virally infected or malignant); one such example is the separation of non-infected pluripotent hematopoietic stem cells from other infected hematopoietic cells and using the isolated, noninfected cells to regenerate a population of uninfected cells which may be used to treat a patient.

DESCRIPTION OF THE DRAWINGS

FIG. 9b, FIG. 9c, FIG. 9d and FIG. 9e show several views of embodiments of the isolation chamber mounted on a table on which is also mounted 4 laser towers.

FIG. 10 is an exploded view of the isolation chamber shown in FIG. 9a;

FIGS. 21a, 21b and 21c show several views of an embodiment of an illumination frame and associated elements.

DETAILED SPECIFICATION

Figure 1:
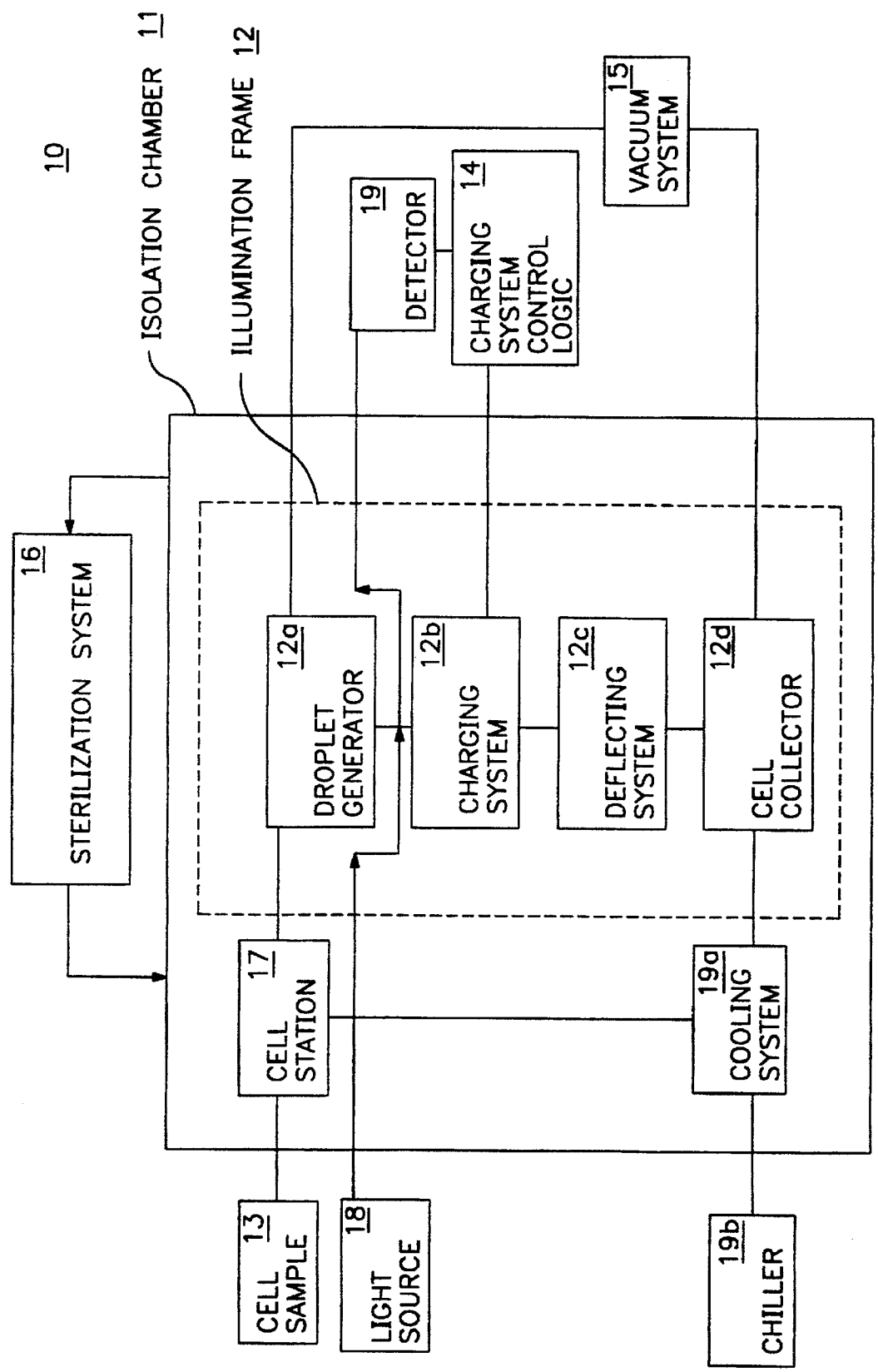
FIG. 1 shows a block diagram of the present invention.

FIG. 1 is a block diagram of an embodiment in the present invention which has the ability to measure properties of biological cells and to sort the cells based on the properties measured, without contaminating the cells. The present invention is a sterile cell sorter 10 which includes several subsystems where, in a typical embodiment, some are located external to an isolation chamber 11 and some are located within isolation chamber 11. In some cases the invention is described in block diagram form where unnecessary detail would obscure the invention; in other cases, specific examples (e.g. specific fluidic connections, specific isolation chamber panel configurations, specific locations of entry and exit ports into the isolation chamber, specific examples of the mechanical isolation between the illumination frame and the isolation chamber, etc.) are described and shown in order to thoroughly describe the invention. It will be appreciated that these specific examples are for the purpose of explanation and that alternative embodiments will be understood by those in the art.

A sterilization system 16, typically located outside isolation chamber 11, sterilizes isolation chamber 11 before cells are measured and sorted within isolation chamber 11 such that the cells may be sorted in a sterile environment. Sterilization system 16 in a typical embodiment injects a sterilant into a first opening in isolation chamber 11, and sterilization system 16 subsequently ventilates isolation chamber 11 by removing the sterilant through a second opening in isolation chamber 11. Typically, the sterilant is a gaseous compound. In an alternative embodiment, a short wavelength ultraviolet (UV) radiation sterilization system located within the isolation chamber may sterilize the chamber by bathing the chamber with UV radiation.

Within isolation chamber 11 is an illumination frame 12 where the properties of cells are measured and the cells may be sorted depending on the values of the properties measured. A droplet generator 12a within illumination frame 12 receives biological cells from a cell station 17, which receives its sample of cells from a cell sample 13 typically located outside isolation chamber 11. The cells within cell station 17 may be cooled by a cooling system 19a which is coupled to a chiller 19b, located outside isolation chamber 11. Chiller 19b generates a coolant which flows through cooling system 19a to keep cooling system 19a cool. In some embodiments, a cooling system may not be necessary; generally, a larger sample volume requires cooling.

After leaving droplet generator 12a, the cells flow in a substantially single file through a measuring region. It will be appreciated that at times several cells will become agglutinated and thus will not pass through in a substantially single file and this circumstance will be detected using conventional flow cytometry coincidence detection circuitry and these cells will not be selected for separation or sorting. A light source 18 provides a laser beam (or several laser beams or, in an alternative embodiment, a beam or beams of light from an arc lamp or several arc lamps) which intersects the cells in the measuring region and a detector 19 collects fluorescent light which is emitted from the cells labeled with fluorescent molecules that pass through the laser beam. After detector 19 collects the fluorescence emitted, detector 19 transforms the flashes of light into electrical pulses, which are measured and recorded by some electronics which are coupled to the charging system control logic 14. A vacuum system 15 removes debris from droplet generator 12a to prevent droplet generator 12a from clogging.

As the cells pass through droplet generator 12a, a charging system 12b electrically charges selected droplets in the conventional manner. The measurements made by the detector system determines whether a particular droplet containing a particular cell is to be charged or not. Typically, the charging system selectively charges the desired droplets and does not charge those droplets not desired (or vice versa). If the measurements of a particular cell requires that particular cell is to be charged, an electrical pulse, generated by the charging system control logic 14, is applied to the unbroken column of fluid, such that the entire column of fluid is temporarily charged. The charging system in one particular embodiment applies a maximum charge of plus or minus 200 volts to the cells at the cell sample inlet 23c (shown in FIG. 2). Eventually after leaving droplet generator 12a, the cells break into a procession of uniform droplets such that almost every droplet contains only one biological cell.

An ultrasonic transducer (e.g. a piezoelectric crystal) is acoustically coupled to the exit orifice of droplet generator 12a to vibrate the generator at a high frequency, as is known in the art, to generate a uniform procession of droplets. It is noted that some in the art may use the term droplet generator to mean the ultrasonic transducer by itself rather than the assembly of the nozzle, ultrasonic transducer and the nozzle holder where the sheath fluid is mixed with the fluid carrying the sample of cells; in this description, the term droplet generator means the assembly of the nozzle, ultrasonic transducer and the nozzle holder. When the droplet (containing that particular cell) is generated, that droplet becomes independently charged and, the unbroken column of fluid returns to its neutral (or grounded) state until the charging system, which depends on measurements made by the detector system, charges another cell.

The procession of droplets then passes through a constant electrostatic deflecting system 12c, which typically includes a positive deflecting plate and a negative deflecting plate that deflects each charged droplet into the appropriate collection receptacle within a cell collector 12d. Those droplets which are not charged fall substantially straight down. In this particular embodiment, deflecting system 12c includes a positive 2500 volt deflecting plate (right side) and a negative 2500 volt deflecting plate (left side) such that the charged droplets are deflected to the left and are collected by a collection receptacle. Furthermore, vacuum system 15 removes waste or unwanted cells from cell collector 12d. In this embodiment, the cells that are not deflected to the left fall straight down into a vacuum tube and are discarded. Preferably cell collector 12d is maintained at a temperature (e.g. 4°–10° C.) to keep the cells alive by a cooling system 19a.

Figure 2:
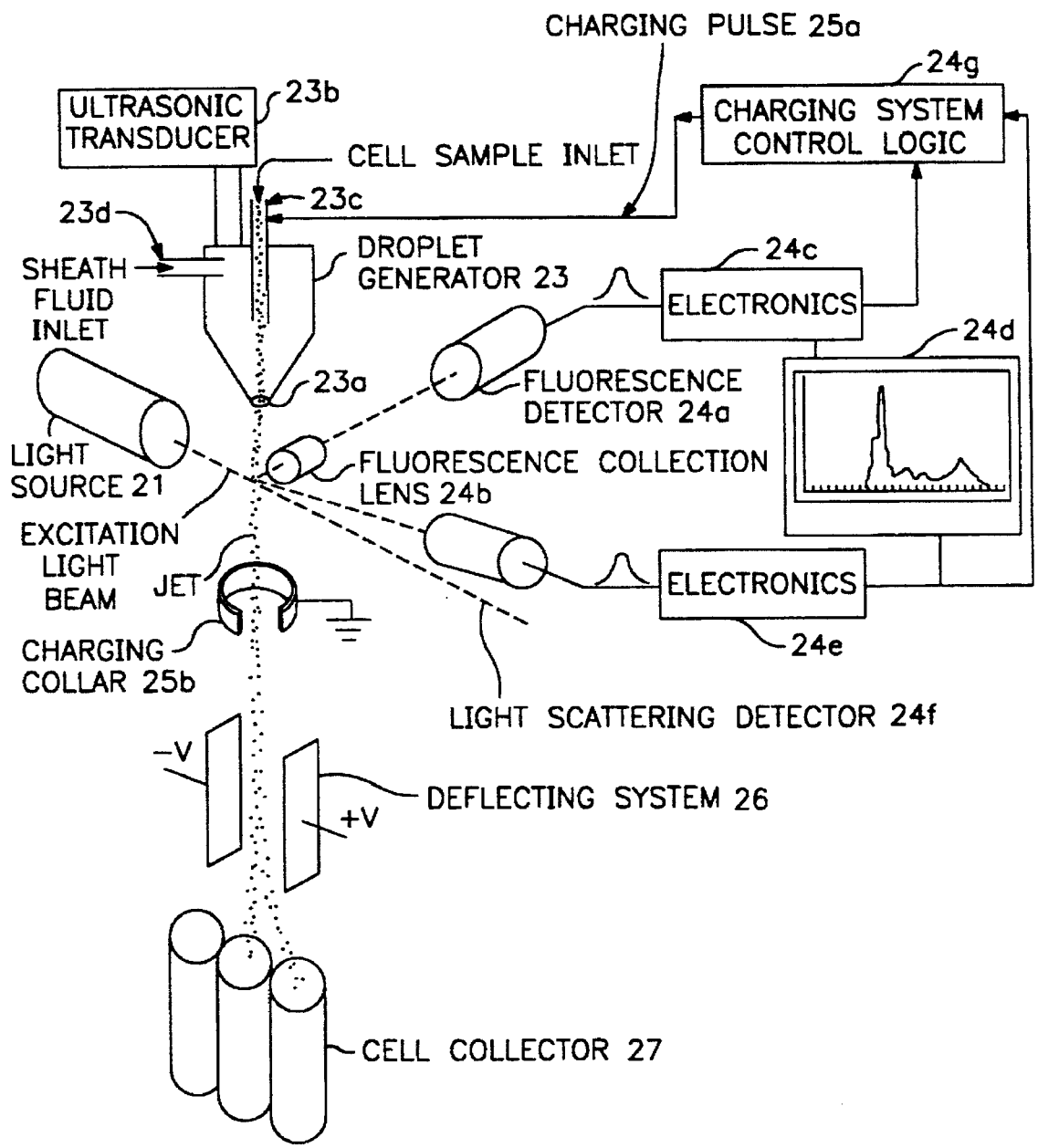
FIG. 2 shows a diagram of the measuring region and its relationship with the light system the droplet generator, the detectors and the charging system control logic.
Figure 3:
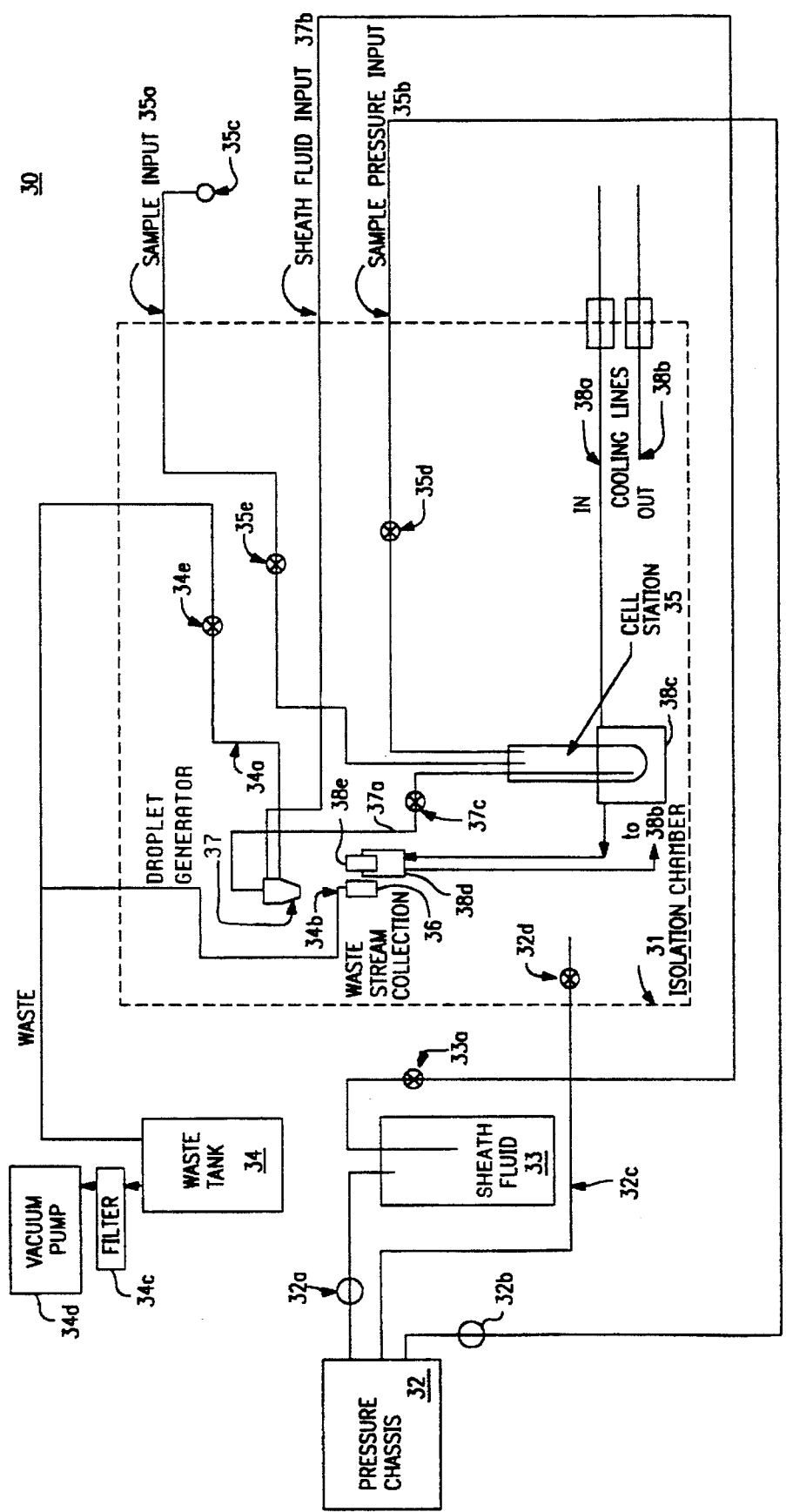
FIG. 3 shows the delivery of fluidics within one embodiment of the present invention.

The delivery of the fluidics in the present invention is further illustrated in FIG. 3. An isolation chamber 31, which corresponds to isolation chamber 11, is shown by the dotted lines. In the embodiment shown in FIG. 3, pressure chassis 32, waste tank 34 and sheath fluid supply tank 33 are located outside of the isolation chamber 31. Within isolation chamber 31 is a droplet generator 37 (which corresponds to droplet generator 23 of FIG. 2) and a cell station 35. Cell station 35 receives a sample of biological cells from a sample input line 35a, a portion of which is located outside of chamber 31, and receives pressurized air from a pressure chassis 32 through sample pressure input line 35b. Pressure chassis 32 usually includes a pressured container of a sterile gas (e.g. sterile gaseous nitrogen ($N_2$)) which is connected to precision pressure regulators 32a and 31b to provide regulated sterile air pressure to the sheath fluid supply tank 33 and to the cell station 35. This air pressure will force the fluids out of the tank 33 and cell station 35 and into the droplet generator 37 at a controlled rate which depends on the regulated air pressures. It will be appreciated that the gas (e.g. $N_2$ or PCA—pharmaceutical clean air or sterile $H_e$) from a gas header or tank may be sterilized by passing it through a sub-micron filter (e.g. 0.22 micron filters from Millipore Corporation). The separate pressure regulators 32a and 31b allow the operator to set a higher pressure in the sheath fluid supply tank 33 relative to the pressure in the cell station 35 such that the ratio of the pressure in sheath fluid supply tank 33 to the pressure in the cell station 35 exceeds 1. In a typical embodiment for a high speed cell sorter according to the present invention, this ratio is about 43/42, with the pressure in the cell station 35 being about 42 psi. In one embodiment, this provides about 23 ml of sheath fluid per 5 minutes of operation from the nozzle. Thus, the sheath fluid will, under a higher pressure from pressure regulator 32a, provide a high pressure flow to hydrodynamically focus the lower pressure flow of the sample of cells from cell station 35.

The cells and the media containing the cells (e.g. a physiological saline buffer solution or a conventional tissue culture media) within cell station 35 may be stirred by a magnetic stirrer. The cells sample is pushed by the air pressure from pressure chassis 32 up through droplet generator input line 37a into droplet generator 37. Sheath fluid from sheath fluid supply 33 is also supplied to droplet generator 37 over sheath fluid input line 37b. The cells received by droplet generator 37 are injected in a conventional manner into a jet of sheath fluid such that each cell is suspended in a substantially single file within the jet of sheath fluid. Note that droplet generator 37 also has an output line 34a connected to a waste tank 34 which is part of the vacuum system. The vacuum system removes debris from the droplet generator by the output line 34a, the end of which is located near the orifice of the droplet generator 37. Waste stream collection receptacle 36 in the cell collector region below the drop generator 37 also has an output line 34b connected to waste tank 34. The waste stream collection receptacle 36 typically corresponds to the cell collector 27 in FIG. 2 which is positioned to collect cells which are not desired/selected, and such cells are considered "waste." Alternatively, both populations of sorted cells may be collected for subsequent use. The vacuum system includes a vacuum pump 34d coupled to the waste tank 34 through a filter 34c; the vacuum pump creates a filtered vacuum in the waste task 34. The filter 34c is a sub-micron sterile filter (e.g. 0.22 micron filter) which is designed to keep a sterile environment in the isolation chamber 31. In one embodiment, the vacuum may be equivalent to about 23 inches of water below atmospheric pressure, as measured by a manometer.

A sterile, dry gaseous nitrogen ($N_2$) source is provided through input line 32c; the input of $N_2$ from this line 32c into the isolation chamber is regulated by a valve 32d (e.g. a pinch valve). This valve allows the operator, typically through the glove ports described below, to control turning on and off the flow of $N_2$ from line 32c into the isolation chamber 31. This source of $N_2$ is provided to allow the operator to dry off spills in the chamber 31 and clogs around the exit orifice of the droplet generator 37. The stream of cells sometimes becomes clogged with a clump of cells; with the orifice being about 70 to 100 µ in diameter, this clogging can occur often, especially in a high-speed cell sorter where the flow rate of the jet is higher than normal (standard speed) cell sorters. These clogs tend to cause erratic squirting of fluids throughout the interior of the isolation chamber, and the sterile, dry gas (e.g. $N_2$) from input line 32c may be used to dry off spills and squirting within the chamber. The portion of input line 32c within the chamber 31 is preferably a long, flexible teflon tubing with the valve 32d located near the end of the tubing where the gas exits the tubing. The length of the tubing is preferably adequate enough to allow the operator to bring the end of the tubing to almost any location within the chamber 31 to dry off spills and/or squirts.

Cooling lines 38a and 38b provide the cooling system with a glycol water mixture at 2–10 degrees Centigrade (typically closer to 2°–4° C.). In this particular embodiment, the glycol/water mixture is about 50% glycol and 50% water. The cooling mixture flows into isolation chamber 31 via cooling line 38a which passes through a first cooling block 38c for cooling the cells in cell station 35 and through a second cooling block 38d for cooling the selected (non-waste) cells in the cell collector 38e before leaving isolation chamber 31 via cooling line 38b. The cooling lines cool, in one embodiment, aluminum or stainless steel cooling blocks 38c and 38d to a low enough temperature to keep the biological cells viable. It will be appreciated that the smaller the cell sample to be sorted, the shorter the sort time will be, an therefore, the requirement for cooling to maintain cell viability is less critical.

The entry or exit of each tube or pipe into the isolation chamber is sealed to preserve sterility after the chamber has been sterilized. Each seal at a wall of the isolation chamber is air tight up to about 1 inch of water above atmospheric pressure (as described below in connection with the helium leakage test). Each tube or pipe is typically connected to a sealed connector at a wall of the isolation chamber, and the particular connections for the various tubes or pipes shown in FIG. 3 are described below in more detail. It will be appreciated that various tubes or pipes shown in FIG. 3 may be sterile, flexible tubing obtained from commercially available sources. Moreover, such sterile tubing may be disposable such that each new cell measuring and/or sorting operation may begin by disposing of the used tubing at various locations and installing new, sterile tubing (and stopcocks or valves) at those locations and then beginning the sterilization cycle shown in FIG. 7. Specifically, referring to FIG. 3, the following tubing in one embodiment may be disposable, sterile tubing: 34a, 35a, 37a and 37b. Also, the stopcocks 34e, 35d, 35e, and 37c may be disposable sterile stopcocks. The sample input line 35a is preferably disposable, sterile tubing with a sterile cap 35c which may be removed in order to connect under sterile conditions (e.g. in a conventional laminar flow hood) the line 35a to a source of the sample of cells to be sorted or measured. This tubing for line 35a and the sterile cap 35c is commercially available. Rather than using sample input line 35a, the sample of cells may be introduced directly into the cell station 35 by a sterile syringe which is introduced into the isolation chamber 11 through the alpha port (which is described below) on the side of the isolation chamber 11. The syringe is used to inject the sample directly into the cell station.

It will be appreciated that the internal surfaces of all of the tubing or pipes should be sterile before beginning a cell sorting operation, and the external surfaces of all tubing or pipes within the isolation chamber 31 should be sterilized (or sterile) before beginning a cell sorting operation. To the extent the tubing or piping is installed with the isolation chamber during the sterilization process described below, the external surfaces of this tubing or piping will be sterilized in this process.

Numerous valves, as shown in FIG. 3, may be used to regulate the flow of fluids through the system shown in FIG. 3. For example, a valve 33a connected to line 37b may be used to regulate the sheath fluid flow in line 37b; also, an in-line filter may be connected in line 37b to filter the sheath fluid before it reaches the droplet generator 37. A valve 35d (or a three-way stopcock) connected in line 35b may be used to regulate the sample air pressure into the cell station 35. Valve 35e (or a one-way stopcock) connected in line 35a may be used to regulate the flow of the solution containing a sample of cells to the cell station 35. A stopcock 34e (or a valve) connected in line 34a between the waste tank 34 and the droplet generator 37 may be used to regulate the vacuum suction at the droplet generator 37. A pinch valve 37c (or alternatively a stopcock) on the cell sample input line 37a, between the cell station 35 and the droplet generator 37, may be used to regulate the flow of the solution containing the sample of cells to the droplet generator 37.

In one alternative embodiment, the valves 34e, 35e, 35d and 37c are electronically controlled pinch valves which pinch down on the tubing. An electric solenoid in each pinch valve is electrically controlled to open or close (i.e. pinch down) the tubing that is surrounded by the pinch valve. The pinch valves (and tubing) may be obtained from NResearch, Inc. of Caldwell, N.J. The use of electrically controlled pinch valves allows the user of the cell sorter to use a switch (e.g. a conventional rotary selector switch) to set the sorter into one of three modes by merely rotating the switching to one of three positions (back flush to remove a clog; measure/sort; shealth on only). This switch is coupled to each of the pinch valves to turn them on or off, as indicated below, depending on the particular mode. The switch is coupled to each pinch valve 34e, 35e, 35d, and 37c to allow for the operation of the sorter in the following modes:

| back flush | measure/sort | shealth on only |
| --- | --- | --- |
| shealth off (33a closed) sample off (35d and 37c closed) vacuum on (35e open) | shealth on (33a open) sample on (35d and 37c open) vacuum off (35e closed) | shealth on sample off vacuum off |

The use of a single switch allows the user to more quickly switch between modes (e.g. when a clog appears) by setting the switch rather than having to insert the user's hands into the gloves and manually set several different stopcocks.

Figure 8:
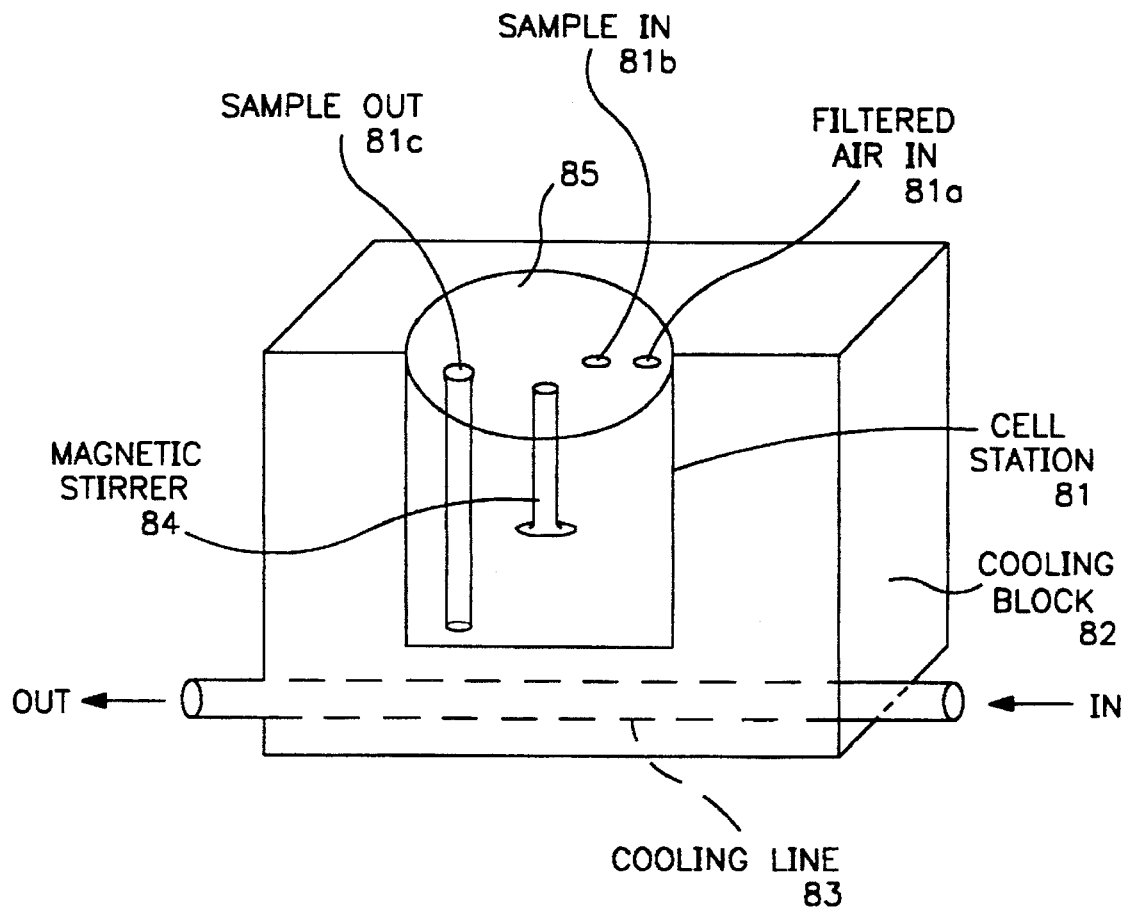
FIG. 8 is a schematic view of the cell station and a cooling block according to one embodiment of the present invention.

FIG. 8 illustrates an embodiment of a cell station 81 being maintained at a cool temperature by cooling block 82; cell station 81 corresponds to cell station 35 in FIG. 3 and cooling block 82 corresponds to cooling block 38c in FIG. 3. Cooling line 83, corresponding to cooling line 38a in FIG. 3, passes through the bottom portion of cooling block 82 where a cooling mixture flows through line 83 to maintain cooling block 82 at a low temperature. The cooling line 83 preferably takes a winding, coil-like path (not shown) through the cooling block 82. Cell station 81 fits into a cavity in the top surface of cooling block 82, as shown in FIG. 8. It is appreciated that cooling block 82 may be cylindrical in shape such that it substantially wraps around cell station 81.

The contents within cell station 81 inside cooling block 82 are visible through an opening in the front of cooling block 82. In other words, cell station 81 is a transparent container which is visible through a window in cooling block 82. By observing the contents of cell station 81 from the outside, the contents flowing into and out of cell station 81 can be better monitored.

Within cell station 81 is a magnetic stirrer 84 suspended from the top 85 of cell station 81. A teflon coated magnetic stirrer 84 stirs the sample of cells in a media received through sample input 81b (via line 35a of FIG. 3). The magnetic stirrer 84 is rotated by a magnet attached to a motor, where the magnet and motor are mounted below the cooling block or inside the cooling block. Conventional, commercially available magnetic stirrers may be used. The air pressure from filtered air pressure received through filtered air input 81a (via line 35b of FIG. 3) eventually pushes the cells out through sample output tube 81c which is coupled to the nozzle holder in the droplet generator by line 37a shown in FIG. 3. It will be appreciated that the sample output tube 81c and the magnetic stirrer 84 typically extend to near to the bottom of the container which constitutes the cell station 81.

Figure 6:
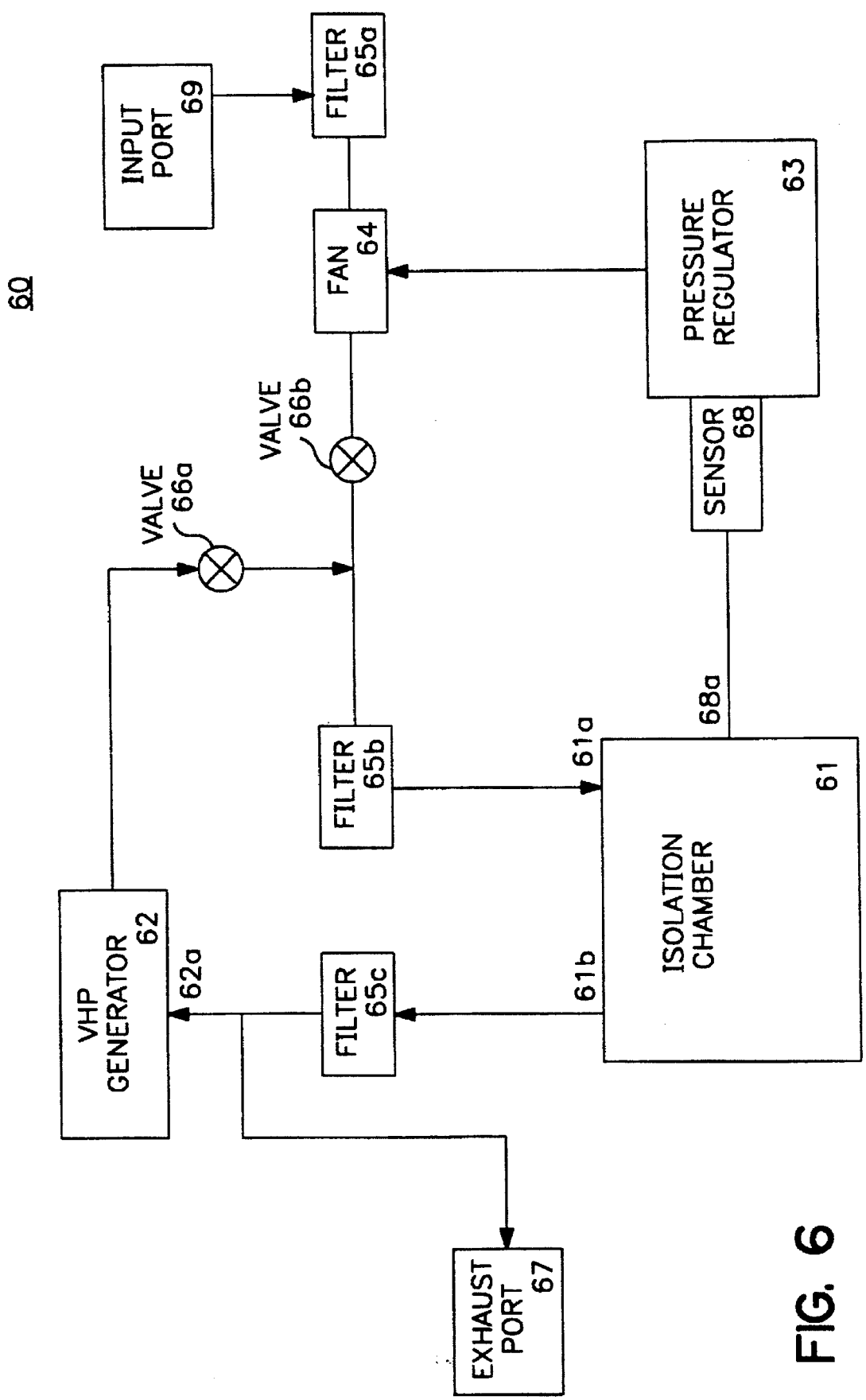
FIG. 6 shows a block diagram of the sterilization system according to one embodiment of the present invention.

The following discussion includes a detailed description of a sterilization system 60 shown in FIG. 6. Sterilization system 60 is used to sterilize the area located within an isolation chamber 61 (which corresponds to chamber 31 in FIG. 3) before measuring and sorting the cells in the present invention, to ventilate the area located within isolation chamber 61 after being sterilized and before measuring and sorting cells, and to maintain the air pressure within isolation chamber 61 above atmosphere pressure during the measuring and sorting of the cells. The sterilization system 60 may also be used to sterilize and then ventilate the area located within isolation chamber after measuring and sorting cells. This sterilization and ventilation, after measuring/sorting cells, protects the user of the cell sorter from any harmful contaminants left from the sample in the previous measuring/sorting of cells. VHP generator 62 used in this embodiment is commercially available and is manufactured by Amsco (Series 1000) and the assembly coupling isolation chamber 61 with VHP generator 62 is commercially available and is manufactured by La Calhene.

VHP generator 62 generates a sterilant known as vapor hydrogen peroxide (or VHP) which is injected into isolation chamber 61, after isolation chamber 61 has been sealed shut, through input 61a when a valve 66a (which may be a cap) is open and a valve 66b is closed and the exhaust port 67 is closed. The sterile hydrogen peroxide vapor passes through a filter 65b (e.g. a sterile sub-micron (e.g. 0.22 micron) pore filter such as those commercially available from Millipore Corporation) before entering isolation chamber 61. The hydrogen peroxide vapor may circulate in a closed loop for a period of time from the VHP generator 62 into the isolation chamber 61 through input 61a and back to the VHP generator 62 through output 61b. After the hydrogen peroxide vapor sterilizes the inside of isolation chamber 61, VHP generator 62 ventilates isolation chamber 61 to remove residual VHP by injecting sterile, filtered air (without VHP) into isolation chamber 61 through input 61a. As the air pressure inside isolation chamber 61 increases above two inches of water (slightly above atmospheric pressure), the hydrogen peroxide vapor and air mixture flow out output 61b of isolation chamber passing through a sterile sub-micron pore filter 65c and eventually returning to VHP generator 62. During the sterilization and ventilation process the exhaust port 67 is closed, typically by placing a tight cap over this port. During the ventilation process, the air and/or hydrogen peroxide vapor removed from the isolation chamber 61 via output 61b and filter 65c is delivered to the VHP generator 62 where the hydrogen peroxide vapor is destroyed while fresh, sterile air without hydrogen peroxide vapor is introduced into isolation chamber 61 via filter 65b and input 61a thereby flushing any hydrogen peroxide vapor out of chamber 61.

After isolation chamber 61 is sterilized and ventilated, the present invention may measure and sort cells. However, sterilization system 60 should maintain a positive air pressure slightly above atmospheric pressure (approximately 2 inches of water above atmosphere pressure in one embodiment) to prevent air from leaking into isolation chamber 61 in the event of a leak in isolation chamber 61. If the pressure within isolation chamber 61 is slightly above atmospheric pressure and there is a leak in isolation chamber 61, the air inside isolation chamber 61 will be pushed out by this positive pressure rather than having air sucked into isolation chamber 61, thereby continuing to maintain sterility. Note that at this point, VHP generator 62 is turned off and the hoses coupling VHP generator 62 to openings 61a and 61b in isolation chamber 61 are typically removed and furthermore, exhaust port 67 is opened, valve 66a is closed and valve 66b is opened. Thus, at this point, the connection from output 61b to input 62a of the VHP generator does not exist, and the air from the isolation chamber 61 exits to the atmosphere through filter 65c and exhaust port 67.

Pressure regulator 63 is coupled to a pressure sensor port 68a located on isolation chamber 61 and the pressure regulator 63 includes a pressure sensor 68. In one particular embodiment, pressure sensor 68 is coupled to isolation chamber 61 by port 68a and is coupled to a pressure regulator 63 which monitors the air pressure within chamber 61 and regulates the pressure to maintain the higher than atmospheric pressure (described above) within the chamber 61. If pressure sensor 68 senses that the air pressure within isolation chamber 61 is too low, then pressure regulator 63 causes a fan 64 to increase its speed, thereby drawing in air through input port 69. If pressure sensor 68 determines that the air pressure inside isolation chamber 61 is too high, pressure regulator 63 reduces the speed of fan 64 and may eventually stop fan 64 while air flows out of isolation chamber 61 through opening 61b, filter 65c and exhaust port 67.

In other words, pressure regulator 63 controls the speed of fan 64 such that the appropriate amount of filtered air can be drawn into isolation chamber 61 to maintain a relatively constant positive air pressure within isolation chamber 61 (e.g. the air pressure within chamber 61 is maintained at 2 inches of water or slightly above atmospheric pressure). Air enters sterilization system 60 through input port 69 and passes through a filter 65a, fan 64, valve 66b and sub-micron pore filter 65b before entering isolation chamber 61 through input 61a. Air flowing out of isolation chamber 61 passes through a sub-micron filter 65c and exits sterilization system 60 through exhaust port 67. Air continuously flows through isolation chamber 61, entering through input 61a and leaving through 61b while a relatively constant pressure within isolation chamber 61 is maintained (above atmospheric pressure). In an alternative embodiment, the pressure regulator 63 may reverse the direction of the fan 64 and control the fan's speed so that a negative pressure (i.e. a pressure lower than atmospheric pressure) is maintained in the chamber 61. This alternative embodiment may be used to prevent escape of contaminants (e.g. infected blood samples) from the chamber 61 in order to protect the user of the cell sorter.

Figure 7:
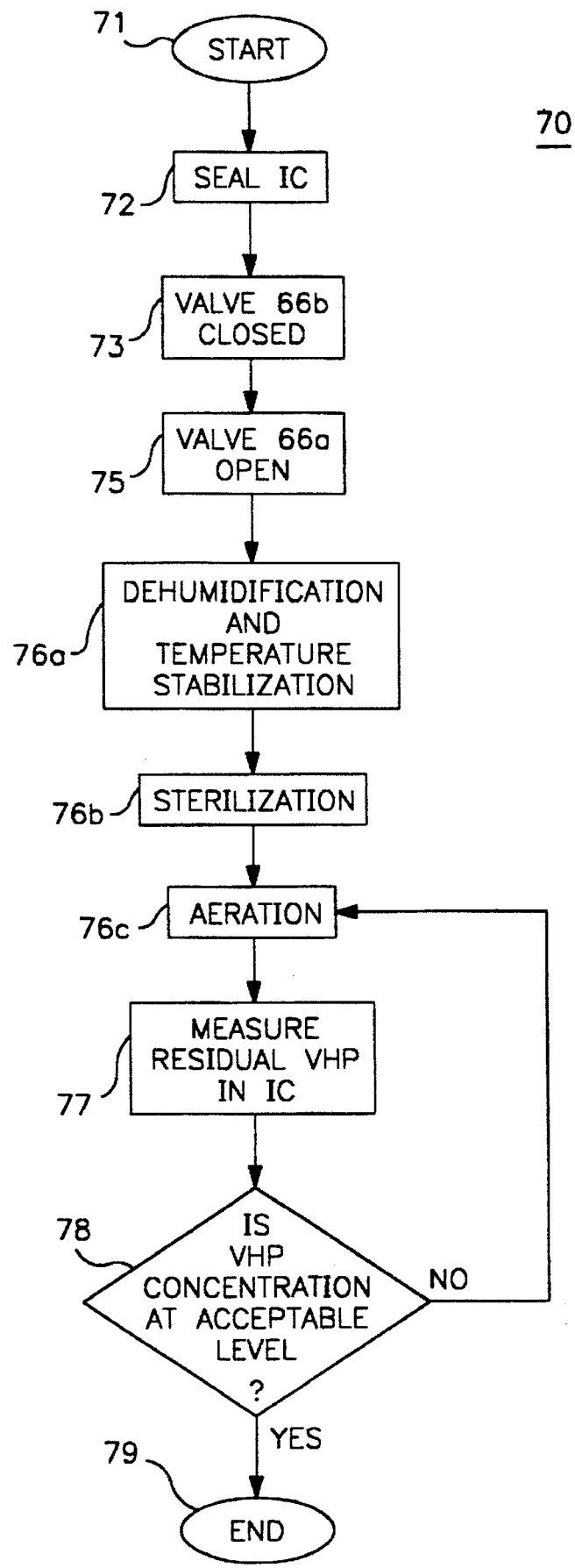
FIG. 7 is a flow chart of the sterilization method according to one embodiment of the present invention.

Referring to FIG. 7, flow chart 70 describes the process involved in sterilizing and ventilating isolation chamber 61. The flow chart starts at step 71 and ends at step 79. The first step 72 is to seal isolation chamber 61 to prevent contaminants from entering into isolation chamber 61. This step involves closing the door to isolation chamber 61 and sealing all openings in the walls of isolation chamber 61.

To ensure that isolation chamber 61 is leakproof before sterilizing it, a leakage test is performed on isolation chamber 61. This test may be performed before each sterilization or only before the first sterilization of the chamber. Preferably, isolation chamber 61 is filled with helium until the air pressure within isolation chamber 61 is at an air pressure greater than atmospheric pressure. The helium pressure within the isolation chamber is measured by a conventional manometer located outside isolation chamber 61. In this particular embodiment, the manometer (manufactured by Dwyer Corp.) is attached to the outside of the left panel of isolation chamber 61. A 3/16 inch barb, for measuring the air pressure inside isolation chamber 61 is connected to a 1/8 inch pipe outside isolation chamber 61. The 1/8 inch pipe is attached to the manometer which displays the air pressure within isolation chamber 61. Helium is inputted into isolation chamber 61 until a pressure of one inch of water above atmospheric pressure is measured by the manometer. Once isolation chamber 61 is filled with helium up to the appropriate pressure level, the amount of helium leaking out of isolation chamber 61 is measured by using a conventional helium detector. The operator physically scans the external surface of isolation chamber 61 with the helium detector to measure the helium leakage. Isolation chamber 61 is considered leakproof if the helium leakage is less than $3 \times 10^{-3}$ milliliters per second. A more detailed description of an embodiment of isolation chamber 61 will be provided below in conjunction with the discussion of FIGS. 9a and 10.

Prior to step 73 but after step 72, a temperature equilibration step may occur as described below. Alternatively, it may occur with the dehumidification step described below. In step 73 valve 66b is closed and in step 75, valve 66a is opened and exhaust port 67 is closed. Once valve 66a is opened, VHP generator 62 injects air and/or hydrogen peroxide vapor into isolation chamber 61 in accordance with steps 76a–76c.

Dehumidification of isolation chamber 61 occurs in step 76a by injecting dry, sterile filtered air from VHP generator 62 into the chamber 61. This step is necessary to ensure that the hydrogen peroxide vapor does not decompose inside isolation chamber 61. It is advantageous to keep the hydrogen peroxide in its vapor state since the hydrogen peroxide is most effective as a sterilant in its vapor form and furthermore, to prevent the condensed hydrogen peroxide vapor from getting the optics inside the isolation chamber 61 wet. A temperature equilibration step is typically performed either before step 73 or during step 76a. This temperature equilibration step involves allowing the internal temperature of the isolation chamber 61 to substantially equilibrate with the temperature of the room containing the isolation chamber 61. Typically, the VHP generator 62 is also in the same room and is injecting, during the dehumidification, sterile, desiccated air, obtained from the room, into the chamber in order to dehumidify and to equilibrate the temperatures.

Once isolation chamber 61 is dehumidified and the internal temperature of the chamber 61 has stabilized to be essentially equal to the temperature of the room containing the chamber 61 (which room typically also includes the VHP generator 62), isolation chamber 61 is sterilized in step 76b. During sterilization, VHP generator 62 injects vapor hydrogen peroxide in a mixture with sterile, dry filtered air into isolation chamber 61 until the hydrogen peroxide vapor concentration inside isolation chamber 61 is high enough and has been circulating inside isolation chamber 61 long enough to effectively kill all bacteria and other living contaminants inside isolation chamber 61. In a typical embodiment the VHP concentration is maintained for about one to one and one-half hours. In one embodiment, 3.2 grams of vapor hydrogen peroxide per minute are injected into the isolation chamber 61 and are circulated through the chamber for about 1 to 1½ hours; in this embodiment, a concentration of 1.27 milligrams per liter at 25 SCCM (standard cubic centimeters per minute) is maintained in the isolation chamber 61 for 1 to 1½ hours.

The next step 76c involves ventilating isolation chamber 61 in order to reduce the hydrogen peroxide vapor concentration to a negligible level. At this point, output 61b of isolation chamber 61 is opened such that the hydrogen peroxide vapor inside isolation chamber can be returned to VHP generator 62 through input 62a to be decomposed and discarded.

According to step 77, the residual hydrogen peroxide vapor inside isolation chamber 61 is measured until the hydrogen peroxide vapor is at as acceptable level as in step 78. If the hydrogen peroxide vapor is not at an acceptable level, then the step 76c is repeated and isolation chamber 61 continues to be aerated. After this final step, isolation chamber 61 is sterile and can be used to measure and sort the biological cells. For more information, refer to AMSCO VHP Generator Series 1000 equipment manual published Jun. 15, 1993.

It will be appreciated that the internal temperature of chamber 61 be preferably maintained at room temperature even after sterilization and ventilation in order to prevent condensation of liquids (e.g. water) onto the optics contained within chamber 61.

Figure 4:
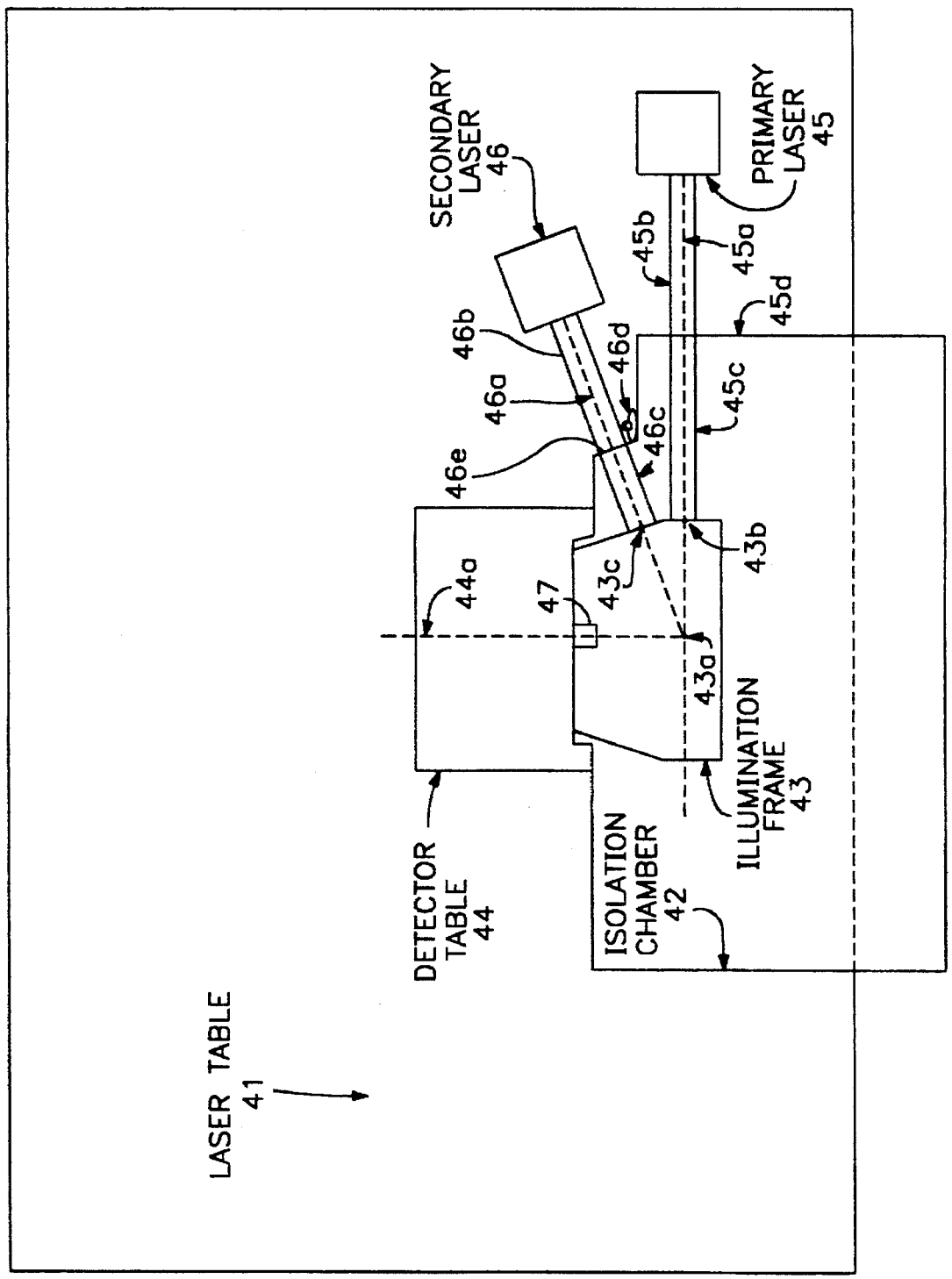
FIG. 4 shows a top view block diagram of the laser table and associated elements according to one embodiment of the present invention.

FIG. 4 is a view of an embodiment of the present invention which illustrates the positioning of an isolation chamber 42 (including illumination frame 43), a detector table 44, and a primary and secondary laser source 45 and 46, respectively, on top of laser table 41. Since laser table 41 supports primary laser source 45 and secondary laser source 46, it is referred to as a "laser" table (often a heavy, stable table), and it is also used to support isolation chamber 42 and detector table 44 in this particular embodiment. As shown in FIG. 4, isolation chamber 42 is positioned on top laser table 41 with the front portion of isolation chamber 42 extending beyond the top surface of laser table 41. In this particular embodiment, isolation chamber 42 extends approximately six inches beyond the top surface of the laser table 41. By extending isolation chamber 42 beyond the top surface of laser table 41, easier access to workspace within isolation chamber 42 is provided. Isolation chamber 42 corresponds to the isolation chamber 31 and 61 of FIGS. 3 and 6 respectively.

Figure 21C:
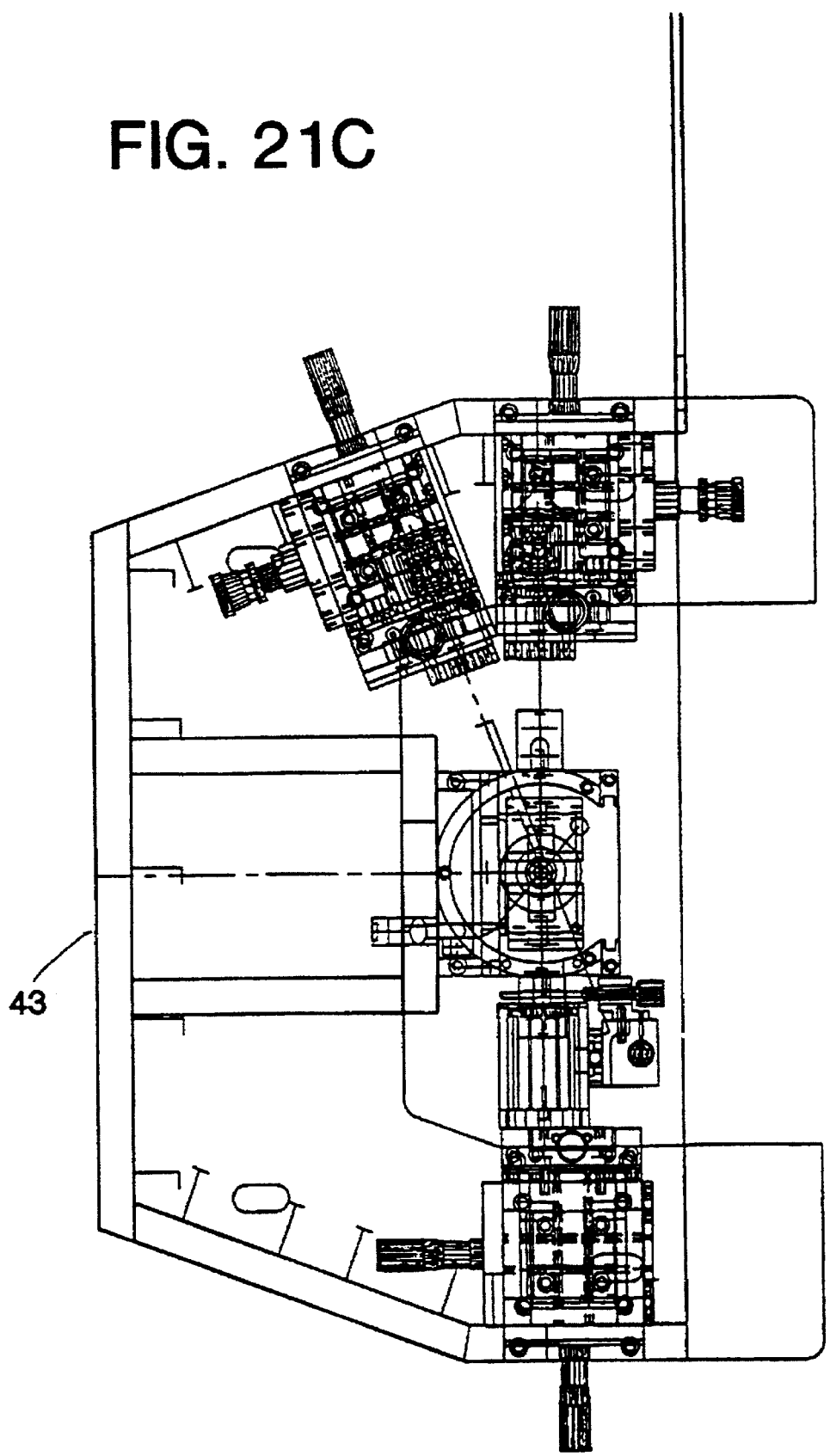

Located within isolation chamber 42 is illumination frame 43, which is positioned near one of the back panels in isolation chamber 42. FIGS. 21a, 21b and 21c show various views of an embodiment of an illumination frame 43. Detector table 44 supports a microscope objective lens 47 providing a magnification power in one embodiment of 40X, which extends along an optical path 44a. Detector table 44 is positioned close to the back of isolation chamber 42 so that a stainless steel tubing surrounding the objective lens 47 is inserted towards an opening in the back panel of isolation chamber 42 and towards the measuring region inside illumination frame 43. Detector table 44 also typically supports in some embodiments various detectors (e.g. fluorescent and light scattering detectors as in FIG. 2) and their associated optics (e.g. collecting lenses, mirrors, filters and measuring slits). It will be appreciated that these detectors and their associated optics normally view the measuring region of the jet (where the stream of cells in the jet intersect the light source's beam) through the objective lens 47. As described above, the illumination frame 43 typically supports, in the conventional manner of cell sorters, the droplet generator 23 and some of the optics for the illumination beams of the light sources, and some of the optics for the detectors (e.g. the objective lens 47) and thus the illumination frame supports numerous components which should be precisely aligned to ensure the intersection of the stream of cells in the jet with the beams of light from the light source(s) and to ensure the reception by the detector(s) of any emitted fluorescence or scattered light from the stream of cells in the jet.

Figure 9A:
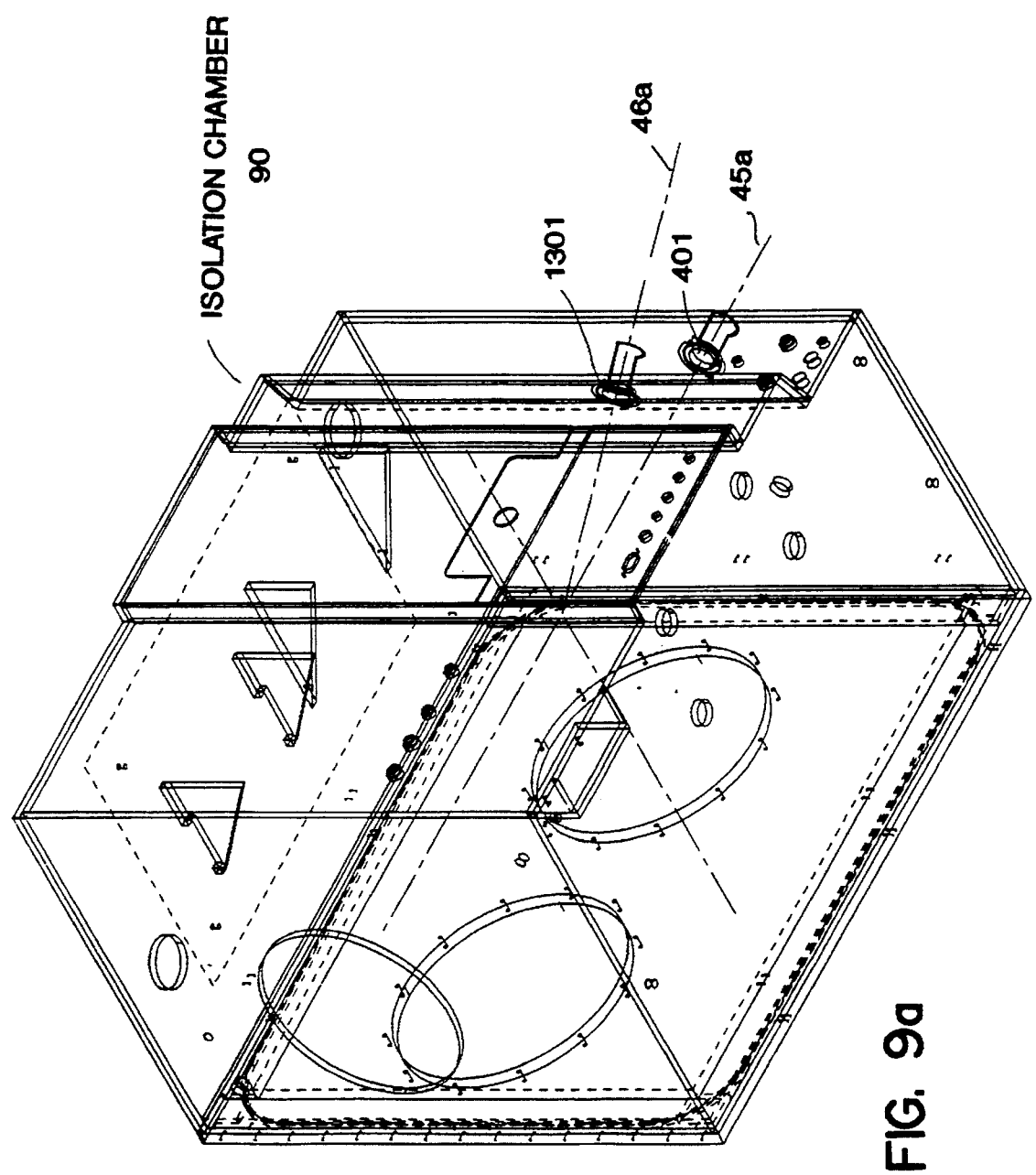
FIG. 9a is a detailed schematic of one embodiment of the isolation chamber.
Figure 9B:
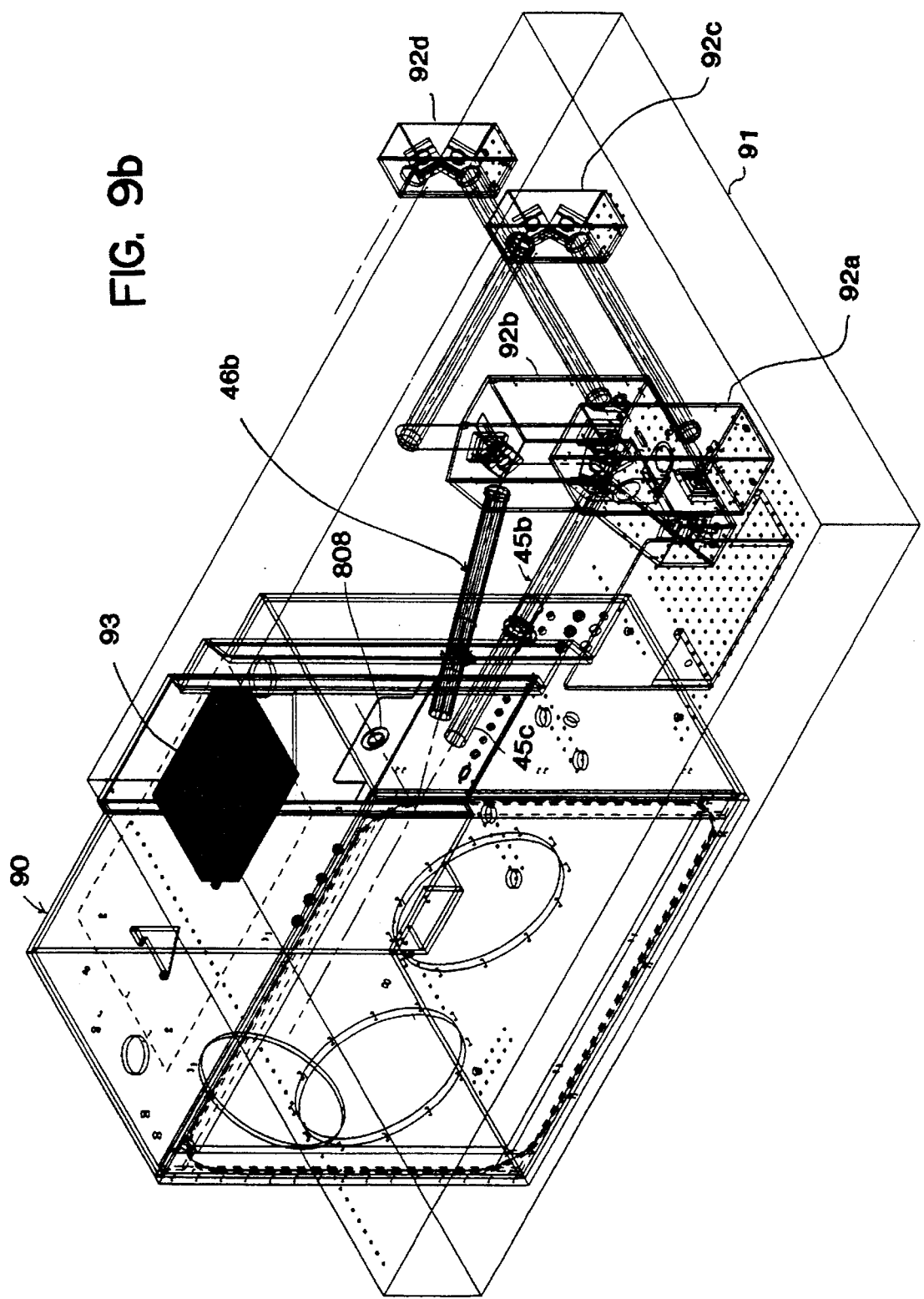
Figure 9E:
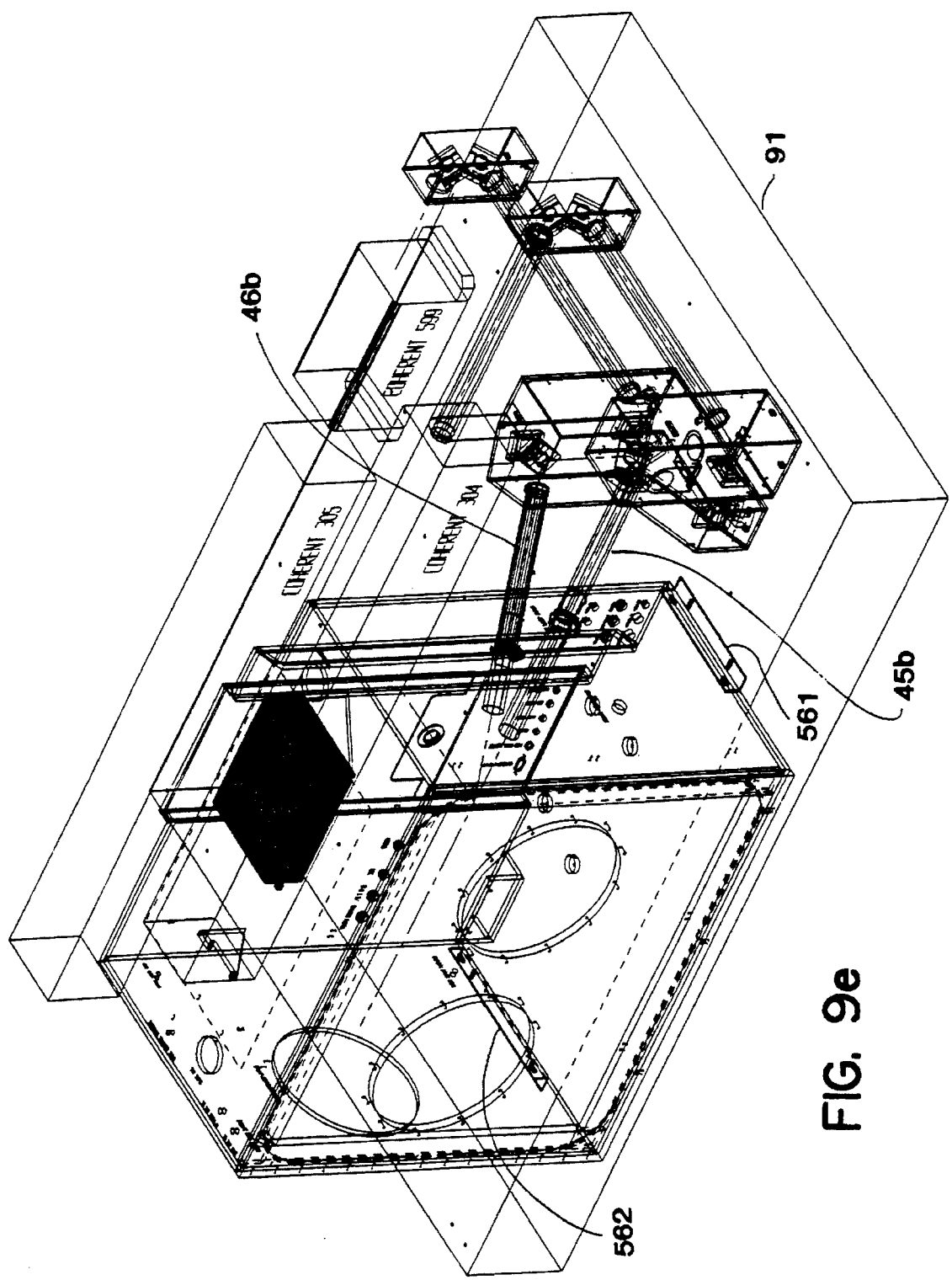

On one side of isolation chamber 42 is a primary laser source 45 and secondary laser source 46; it will be appreciated that these sources may be located on other locations on the laser table (e.g. in the left, back corner of the table, viewed as shown in FIG. 4), and the beams of light from these sources may be directed into the isolation chamber 42 through conventional arrangements of mirrors in "laser towers" (see, e.g. FIGS. 9b and 9c). It will also be appreciated that other light sources (e.g. arc lamps) may be used as is known in the art. Primary laser 45 is coupled to the illumination frame by a two-section primary laser safety pipe 45b and 45 c, one section 45b of which extends to an exterior surface of a wall of isolation chamber 42 and the other section 45c extending from the corresponding location on the interior surface of the wall of the isolation chamber to close to the measuring region. Secondary laser 46 is similarly coupled to the illumination frame by a two-section secondary laser safety pipe 46b and 46c, one section 46b of which also extends to an exterior surface of a wall of isolation chamber 42 and the other section 46c extending from the corresponding location on the interior surface of the wall of the isolation chamber to close to the measuring region. The end of the primary and the end of the secondary laser safety pipes which are located within isolation chamber 42 may each be supported by an openings 43b and 43c respectively in illumination frame 43, as shown in FIGS. 21a and 21b. It will be understood that, as is often the case with conventional cell sorters, focusing lenses (e.g. lenses to re-shape the cross-sectional shape of the light beam from a circle to an ellipse) or other optics conventionally associated with the light beam source(s) may be located on and/or supported by the illumination frame 43.

FIG. 4 further illustrates an embodiment where a primary laser beam path 45a is located approximately 90 degrees to the right of optical path 44a, and the secondary laser beam path 46a is located about 70 degrees to the right of optical path 44a. Note that optical path 44a, and primary laser beam path 45a cross one another inside the measuring region, at the point marked 43a. Similarly, optical path 44a and secondary laser beam path 46a cross one another inside the measuring region also near the point marked 43a. This is where the fluorescently labeled cells flow in a substantially single file in a jet (e.g. see the jet in FIG. 2 down toward the cell collector (see FIG. 2)) and pass the primary and secondary laser beams (usually one after the other) in order to emit a fluorescent light which is collected by the optics on detector table 44. As shown in FIG. 2, a forward light scattering detector may also be located off optical axis 45a on the opposite end of the point marked 43a from primary laser 45.

Note that the optical path 46a of the secondary laser 46 enters the isolation chamber 42 at the isolation chamber wall 46e of isolation chamber 42. This wall 46e has an angle 46d, relative to a back panel of the isolation chamber, which is related to the angle between the primary laser and secondary laser beam paths 45a and 46a. As shown in FIG. 4, the back panel is perpendicular to the right side wall 45d of the isolation chamber, and thus the angle 46d=90°+x, where x is the angle between the primary and secondary laser beam paths. In the case where the angle between the paths is 20°, then x=20° and the angle 46d=110°. In other words, the angle between the two walls 46e and 45d will be substantially equal to the angle between the two light source paths. Positioning the wall 46e relative to wall 45d in substantially the manner shown in FIG. 4 ensures that the angle of impingement of the two laser beams onto the walls of the isolation chamber is substantially perpendicular to the respective wall; this minimizes distortion of the beams as they cross the walls and allows the safety pipes to have flat ends. The walls 46e and 45d, which are constructed from plastic, each have optical glass inserted and sealed into holes in the walls where the optical paths and laser safety pipes intersect the walls. The optical glass placed in hole 401 (shown in FIG. 11) in wall 45d and the optical glass placed in hole 1301 (also shown in FIG. 11) in wall 46e minimize distortion of the beams as they cross the wall. It will be appreciated that all 45d corresponds to right panel 400 in FIG. 11 and that wall 46e corresponds to panel 1300. The primary and secondary laser safety pipes, in an alternative embodiment, may each be a single pipe inserted through respective sealed holes in the chamber walls; in this case, the ends of each such pipe within the chamber are sealed with optical glass in order to keep the chamber sealed. It has been found that a single primary laser safety pipe is more difficult to align than two separate sections of the primary safety pipe.

Figure 5A:
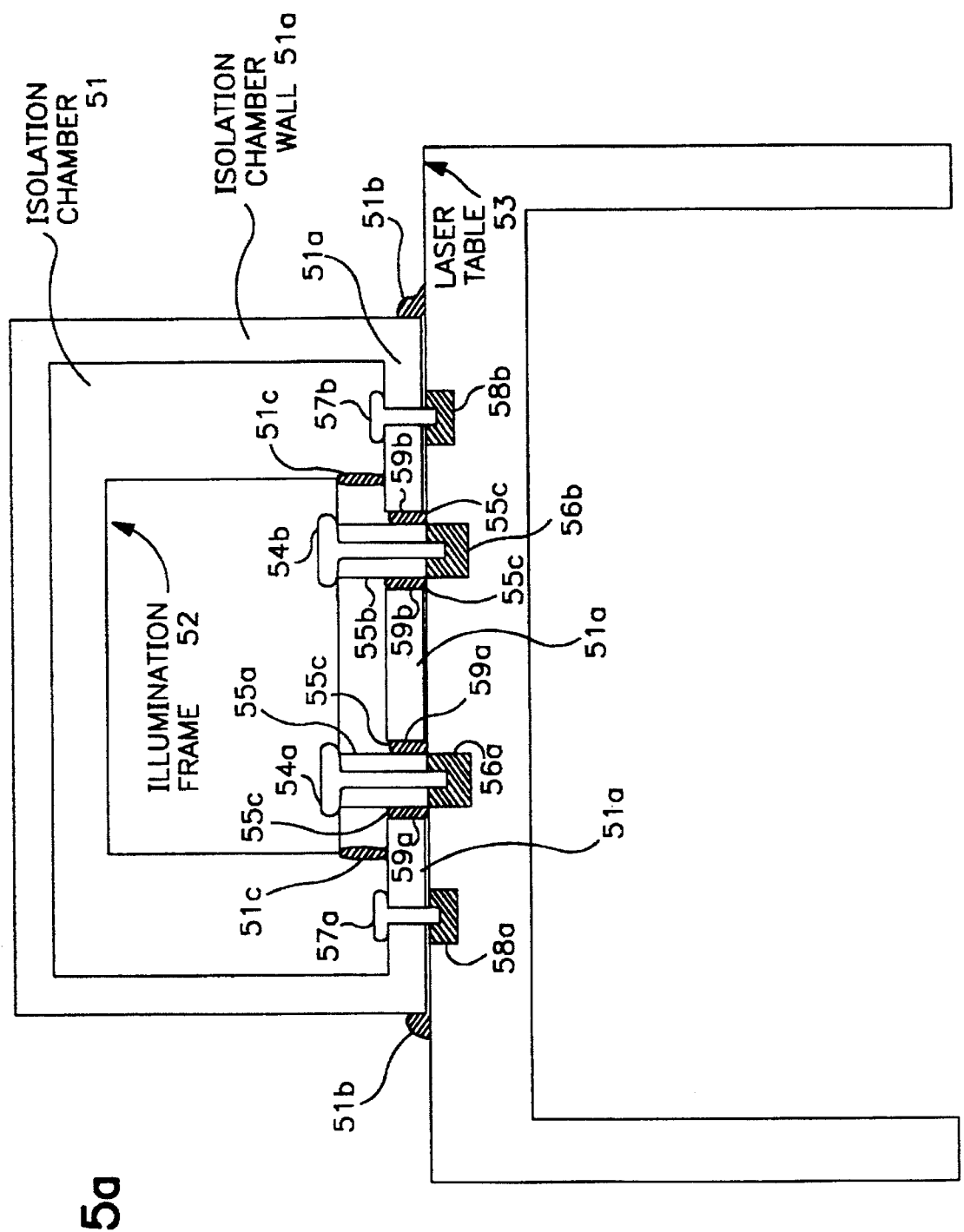
FIG. 5a shows a cross-sectional view of the illumination frame and isolation chamber attached to the laser table according to one embodiment of the present invention.

The mechanical isolation of the illumination frame and its associated components from the isolation chamber will now be described. FIG. 5a illustrates a cross sectional view of an embodiment of an isolation chamber, shown as isolation chamber 51, and an embodiment of an illumination frame, shown as illumination frame 52, positioned on top of a support surface, shown in this embodiment as laser table 53. Although illumination frame 52 is located within isolation chamber 51, it can be mechanically detached and separated from isolation chamber 51 such that it is mechanically isolated to some extent from small vibrations and flexions of the isolation chamber. As shown in FIG. 5a, isolation chamber 51 is bolted to laser table 53 by bolts 57a and 57b which are secured by threaded holes 58a and 58b on the top of laser table 53. Furthermore, illumination frame 52 is bolted to laser table 53 by bolts 54a and 54b. Illumination frame 52 is supported above the table 53 by hollow cylindrical standoffs 55a and 55b which are approximately 12 millimeters high in one embodiment. Cylindrical standoffs 55a and 55b are inserted respectively through openings 59a and 59b in the isolation chamber wall 51a (in one embodiment approximately ⅜ inches thick) and are supported by the top surface of laser table 53. In this example, the bottom surface of illumination frame 52 is about 2½ millimeters above the bottom surface of isolation chamber 51.

In one embodiment, the diameter of each cylindrical standoff is 1 inch in diameter, and the through openings 59a and 59b in the isolation chamber wall 51a in which cylindrical standoffs 55a and 55b are inserted are 1½ inches in diameter. Since the diameter of the through openings 59a and 59b is larger than the diameter of the cylindrical standoffs, flexible silicone 55c is used to fill the gap between each through opening and the cylindrical standoff inserted into isolation chamber 51a wall, thereby providing an airtight seal in isolation chamber wall 51a. By making the diameter of each through opening in isolation chamber 51a wall larger than the diameter of each cylindrical standoff, small movements in isolation chamber 51 do not affect the positioning of illumination frame 52 relative to laser table 53.

Bolts 54a and 54b are inserted through standoffs 55a and 55b, respectively, from the inside of illumination frame 52 through openings in the wall of isolation chamber 51 and secured by threaded holes 56a and 56b, respectively, on the top of laser table 53. Note that bolts 54a and 54b do not touch the internal walls of the hollow cylindrical standoffs 55a and 55b. This additional space surrounding bolts 54a and 54b allows further movement or flexion in isolation chamber 51 without affecting the position of illumination frame 52 relative to the table 53. It is preferable that the optical laser beam paths accurately intersect the microscopic jet of cells (e.g. 20 microns) flowing in the measuring region inside illumination frame 52 and that the detecting optics are aligned also with this region to detect the emitted or changed (scattered) light. Therefore, slight movements of illumination frame 52 may require the user to reposition the primary and secondary laser beams; in alternative embodiments, the objective lens may also be repositioned. These slight movements may occur each time the operator inserts his/her hands in the glove ports (or otherwise uses the gloves) on the front of the isolation chamber. Thus, it becomes apparent that keeping illumination frame 52 as steady as possible relative to the table 53 (which also typically supports the detector table) is advantageous.

Note that in this particular embodiment, flexible silicone 51b, around the perimeter of the bottom panel of isolation chamber 51, may be used to seal the perimeter of the external bottom of isolation chamber 51 to the top surface of laser table 53. Furthermore, flexible silicone 51c is placed around the perimeter of the bottom edge of illumination frame 52 to seal illumination frame 52 to the internal bottom surface of isolation chamber 51. By sealing illumination frame 52 to isolation chamber 51, sheath fluid escaping from the sort flow, cannot leak under illumination frame 52. In one embodiment of the present invention, Silicone 999A, manufactured by Dow Corning, which is bacterial free and growth retardent is used.

Figure 5B:
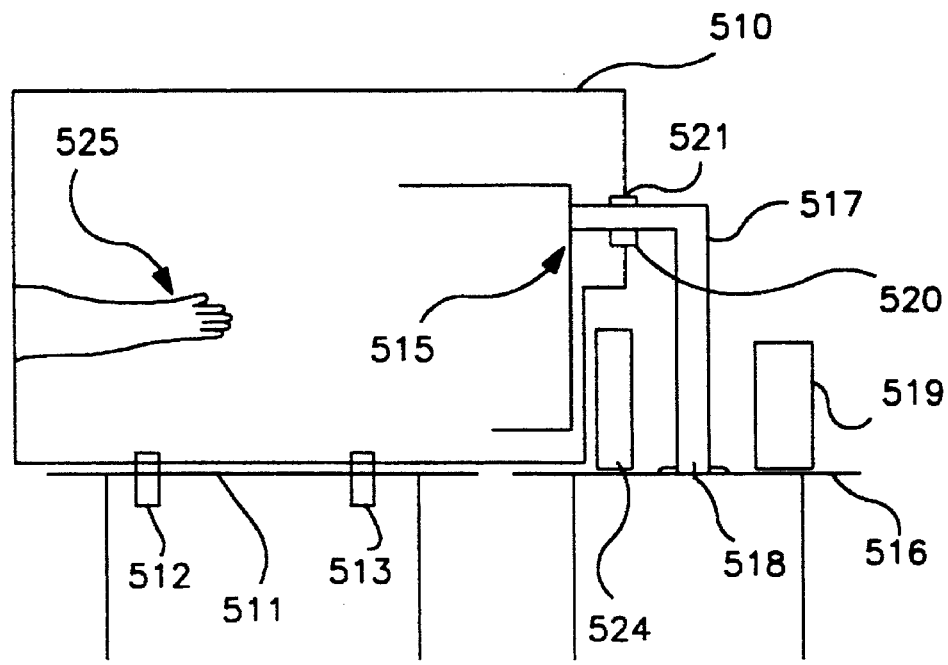
FIG. 5b and FIG. 5c show alternative embodiments of mechanical arrangements between the illumination frame and the isolation chamber
Figure 5C:
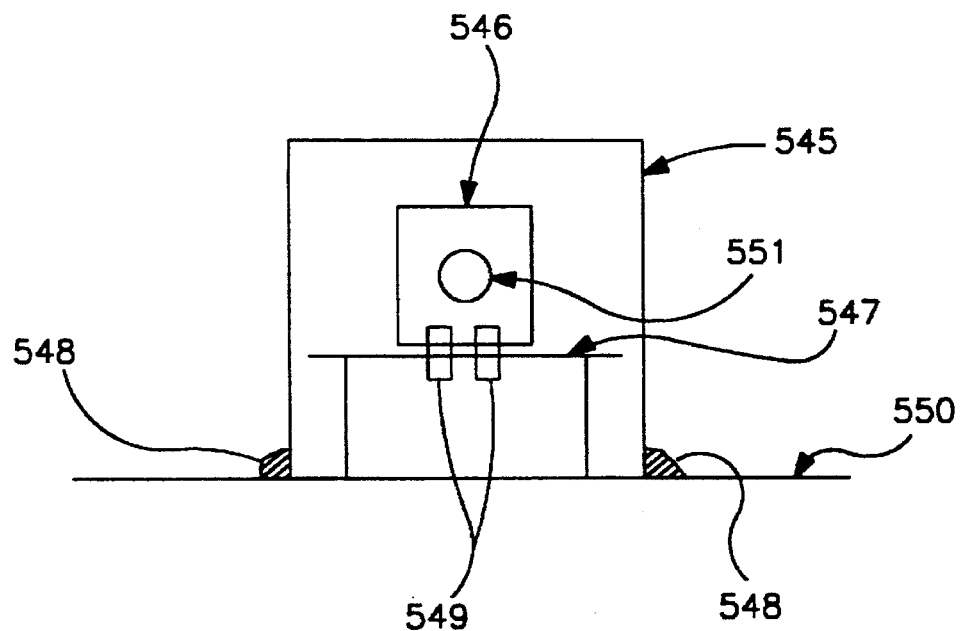
Figure 5D:
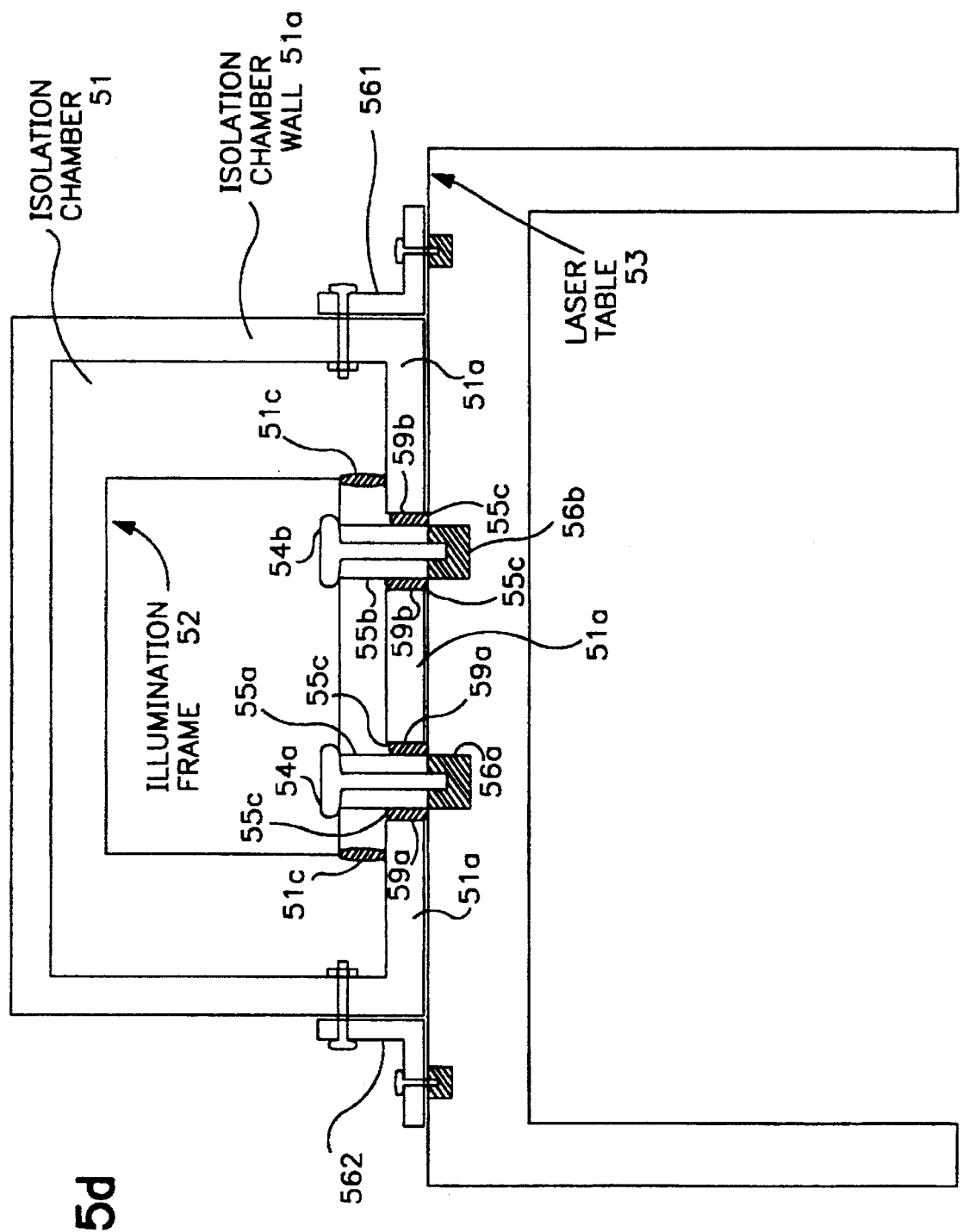
FIG. 5d shows an alternative arrangement for securing the isolation chamber to the laser table.

As an alternative to using bolts 57a and 57b to secure the chamber 51 to laser table 53, the chamber 51 may be secured to the table 53 by angle brackets 561 and 562 on the right and left sides of the chamber 51 as shown in FIG. 5d. In this instance, fewer holes are required on the bottom of the isolation chamber 51.

FIGS. 5b and 5c show two further examples of embodiments wherein the illumination frame is fixedly attached to a supporting surface (e.g. laser table) while being mechanically isolated from the isolation chamber. In the embodiments of FIGS. 5a and 5b, the table and the illumination frame are mechanically secured (e.g. with bolts) together through an opening in the isolation chamber, where the opening is sealed with a flexible, pliant sealant which acts as a shock absorbent. This allows the isolation chamber to be mechanically isolated (at least to the extent of small vibrations and flexions from manipulations of the gloves or the canister, both of which are typically attached to a wall of the isolation chamber) from the illumination frame and the optics and light sources on the supporting surface. In the case of the embodiment of FIG. 5c, the isolation chamber entirely surrounds the illumination frame and at least a portion of the table supporting the illumination frame, although the chamber is not normally the size of a room and is not normally large enough to allow the operator to walk into the chamber and remain in the chamber during normal operation of the cell sorter.

In the embodiment of FIG. 5b, an isolation chamber 510 is mounted on a table 511, which is next to a laser table 516. The isolation chamber is secured to table 511 by two mounting mechanisms (e.g. nut and bolt combinations) and includes a glove port and glove 525 which allows the operator to control the cell sorter. An illumination frame 515 is positioned within the chamber 510 and is mounted to the laser table 516 by an "L" shaped arm 517 which is rigidly attached to the illumination frame 515. The arm 517 is rigidly attached to the table 516 by a securing mechanism 518 (e.g. a nut and bolt combination). The table 516 supports a laser assembly 519 (e.g. a laser source and associated optics, such as laser towers, for directing a light beam to the measuring region within the illumination frame) and typically also supports a detector assembly 524 (e.g. microscope objective lens and associated optics and detectors). The arm 517 projects from the outside of chamber 510 into the inside of chamber 510 through an opening 521 in the chamber's wall, which opening is sealed (to preserve sterility after a sterilization operation) by a flexible sealant 520. The view shown in FIG. 5b is cross-sectional, and thus the sealant is shown above and below the arm 517; it will be understood that the sealant extends around the perimeters of opening 521 and arm 517. It will also be appreciated that one table may be used in place of two tables; for example a heavy laser table may support both the isolation chamber 510 and the arm 517 and illumination frame.

The embodiment of FIG. 5c, shown in cross-sectional view, includes an isolation chamber 545 that rests on a floor 550 of a room. The perimeter of the bottom edge of the chamber 545 is sealed to the floor 550 by a sealant 548. Isolation chamber 545 entirely surrounds the illumination frame 546 which is secured to a table 547 by mounting mechanisms 549. The operator has access to the components within the frame 546 as well as other components of the cell sorter through at least one glove sleeve/port 551 (shown in cross-sectional view a tube which represents the sleeve). A further table (e.g. a laser table) may be placed behind and outside of the isolation chamber 545 and behind the table 547, and this further table may be used to support a laser assembly and a detector assembly. In this case, optical glass inserted into sealed holes in the walls of chamber 545 would be placed in the optical pathway between the optics on this further table and the optics and the measuring region within the isolation chamber. Generally, the embodiment of FIG. 5c provides a very high degree of mechanical isolation between the isolation chamber and the illumination at the expense of a more complicated optical interconnection between the light sources and detectors unless these components are placed within the chamber.

The discussion below focuses on the physical structure of an isolation chamber according to one embodiment of the invention, isolation chamber 90. In this particular embodiment, the panels of the isolation chamber 90 are made of polycarbonate (a particular brand which may be used is referred to as "Lexan"). FIG. 9a is a detailed drawing of isolation chamber 90 with all panels attached together. Note that isolation chamber 90 has numerous openings, all of which need to be sealed in order to create a sterile environment. The specific connectors used with each opening in isolation chamber 90 are identified below. In general, the connectors that are screwed together to form a compression seal are sealed to isolation chamber 90 with teflon tape, and all other connectors use either silicone or a washer to form a seal. As mentioned above, the silicone used in one embodiment of the present invention is manufactured by Dow Corning which is bacterial free and retardant against bacterial growth. The washers used in the present invention are industry standard stainless steel washers in the shape of a ring with the interior hole lined with rubber.

Several further views of embodiments of the isolation chamber of the present invention are shown in FIGS. 9b, 9c, 9d, and 9e. In FIG. 9b, the isolation chamber 90 is mounted on the top surface of the laser table 91, with an overhang portion of the chamber 90 extending beyond the front edge of the table 91. Also mounted on table 91 are four laser towers 92a, 92b, 92c and 92d which contain conventional mirrors which are set up to direct laser beams from two lasers into the laser safety pipes 45b and 46b and thus into the measuring region within the illumination frame in the chamber 90. The two lasers may be mounted on table 91 behind chamber 90 on the back left corner of table 91. In one embodiment, a laser (the primary laser) directs a primary laser beam to tower 92c which, through two mirrors, directs the primary laser beam to tower 92a which, also through mirrors, directs the primary laser beam 45a into the isolation chamber 90 through the primary laser safety pipes 45b and 45c. Also note there are laser safety pipes in which the laser beam is directed from the primary laser (e.g. the pipe between towers 92a and 92c). A secondary laser directs a secondary laser beam to tower 92d which, through two mirrors, directs the secondary laser beam to tower 92b which, also through mirrors, directs the secondary laser beam 46a into the isolation chamber 90 through the secondary laser safety pipes 46b and 46c In FIG. 9c, the isolation chamber 90 is shown (at a different perspective angle) mounted on table 91, and laser safety pipes have been removed to show the beam paths 45a and 46a intersecting at 43a in the measuring region within the illumination frame (not shown). The laser towers 94a, 94b, 94c, 94d are also shown mounted onto table 91 in order to direct the laser beams from the primary and secondary lasers which may be mounted on the left rear corner of table 91 behind the isolation chamber 91. It will be appreciated that increased flexibility in aligning the light source is achieved by having a plurality of laser towers for a laser beam source, each tower having a plurality of mirrors to direct the laser beam to the measuring region. In the embodiments shown in FIGS. 9d and 9e, the isolation chamber is secured to the laser table by angle brackets 561 and 562 with bolts inserted through holes in the angle brackets.

Figure 10:
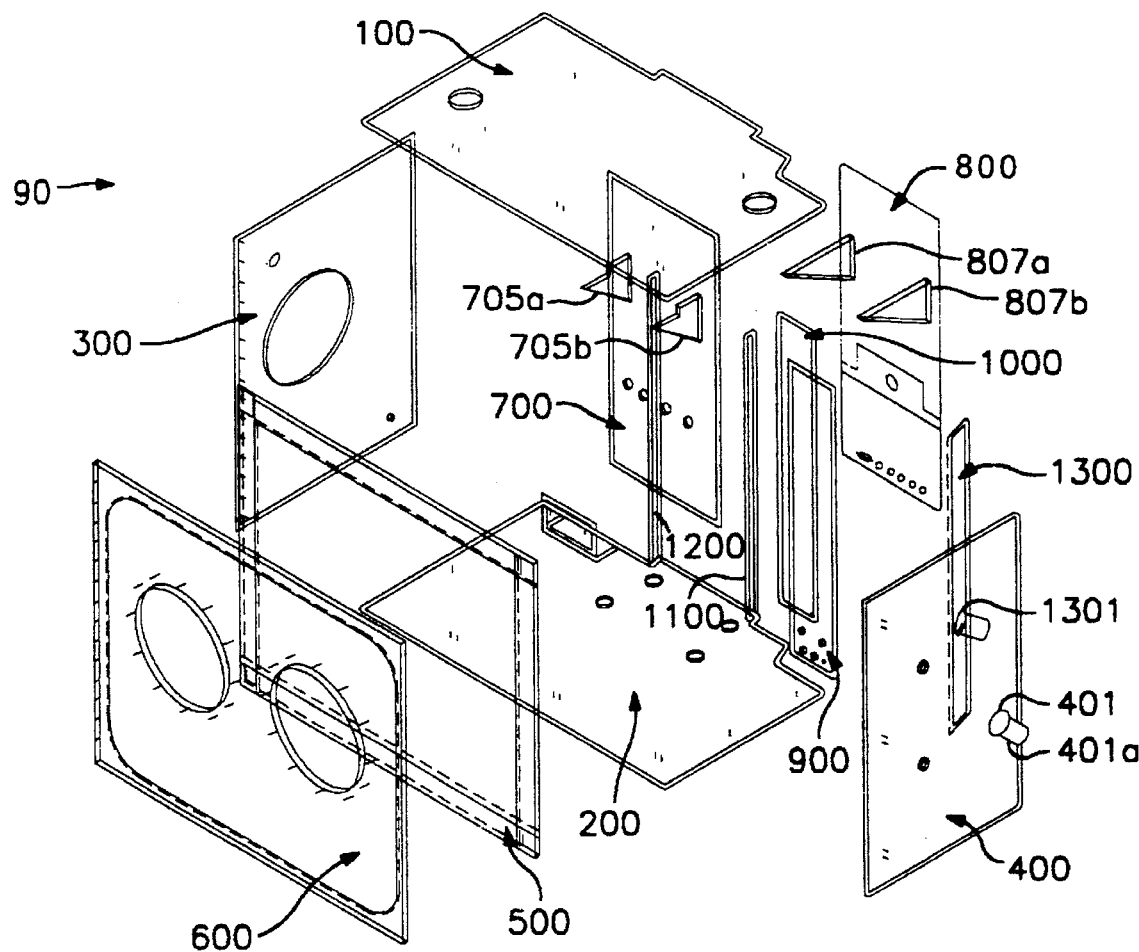

FIG. 10, an exploded view of isolation chamber 90, further illustrates the different panels and sides of one embodiment of isolation chamber 90. According to FIG. 10, panel 100 is the top panel, panel 200 is the bottom panel, panel 300 is the panel for the left side, panel 400 is the panel for the right side, frame assembly 500 along with door 600 form the front panel, panels 700, 800, 900, 1000, 1100 and 1200 are the various back panels, and panel 1300 is a second panel on the right side. The individual panels will be discussed in further detail below.

Figure 11:
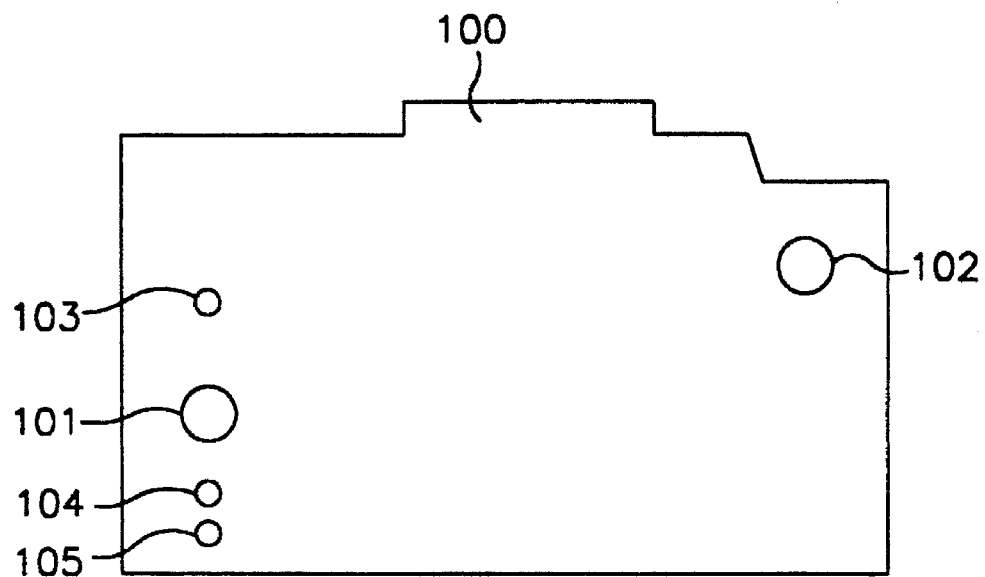
FIG. 11 is a drawing of the top panel in the isolation chamber of FIG. 10.

Starting with a top panel 100 shown in FIG. 11, opening 101 provides an input for a sterilant or sterile, filtered air, and opening 102 provides an output for the sterilant or sterile, filtered air. Openings 101 and 102 correspond to input 61a and output 61b shown in FIG. 6 and are discussed in conjunction with sterilization system 60. Tubes are used to connect the sterilization system to isolation chamber 90 and are sealed to openings 101 and 102 with silicone. Opening 103 corresponds to opening 68a shown in FIG. 6 which connects pressure sensor 68 to pressure regulator 63. In this particular embodiment, pressure sensor 68 and pressure regulator 63 are used to maintain a positive air pressure during the operation of the cell sorter except during the sterilization process when VHP generator 62 is in operation. When VHP generator 62 is injecting hydrogen peroxide vapor into isolation chamber 90, a second pressure sensor inserted through opening 104 and a third pressure sensor inserted through opening 105 are used to regulate the air pressure and display the air pressure within isolation chamber 90. The second pressure sensor is connected to a pressure regulator on VHP generator 62 and the third pressure sensor is connected to a pressure display on VHP generator 62.

Figure 12:
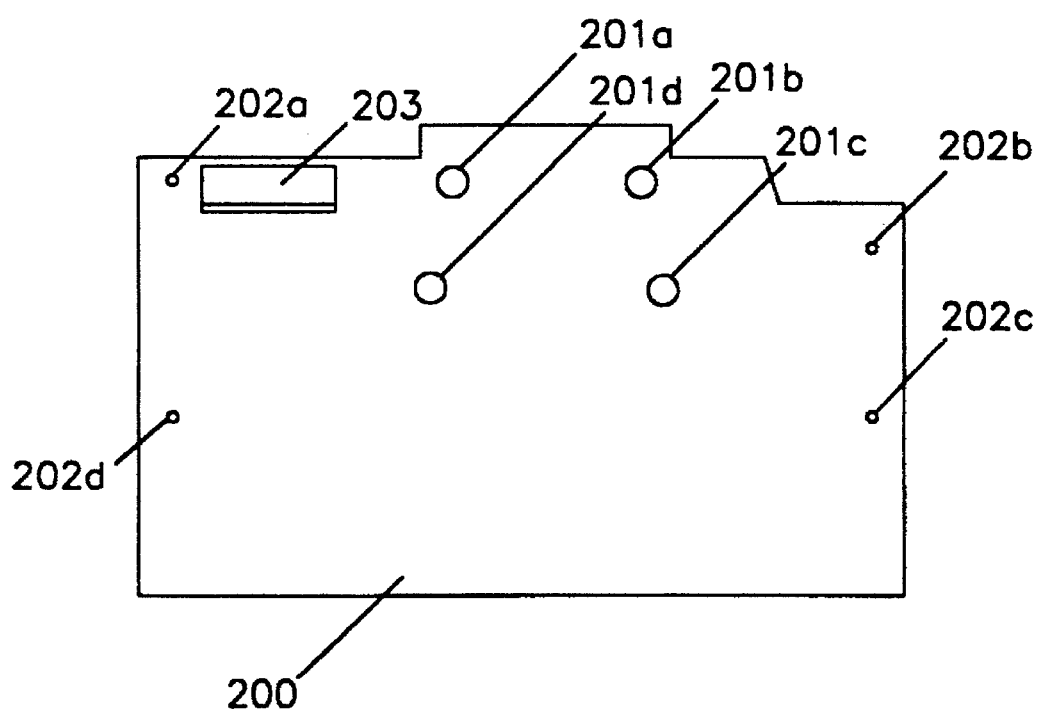
FIG. 12 is a drawing of the bottom panel in the isolation chamber of FIG. 10.

A bottom panel 200, shown in FIG. 12, includes a total of eight openings. Openings labeled 201a–201d are used for bolting the illumination frame to the laser table and openings labeled 202a–202d are used for bolting the isolation chamber to the laser table, as described in conjunction with FIG. 5a. Alternatively, in the embodiment where the chamber is secured to the table by angle brackets 561 and 562, openings 202a through 202d do not exist on panel 200 (rather they appear on the panels 300 and 400). A camera power supply brace is labeled 203. Furthermore, silicone around the perimeter of bottom panel 200 is used to seal the isolation chamber to the laser table; this extra seal is a precaution against leakage due to the openings (e.g. the openings for standoffs of the illumination frame) in the bottom panel 200.

Figure 13:
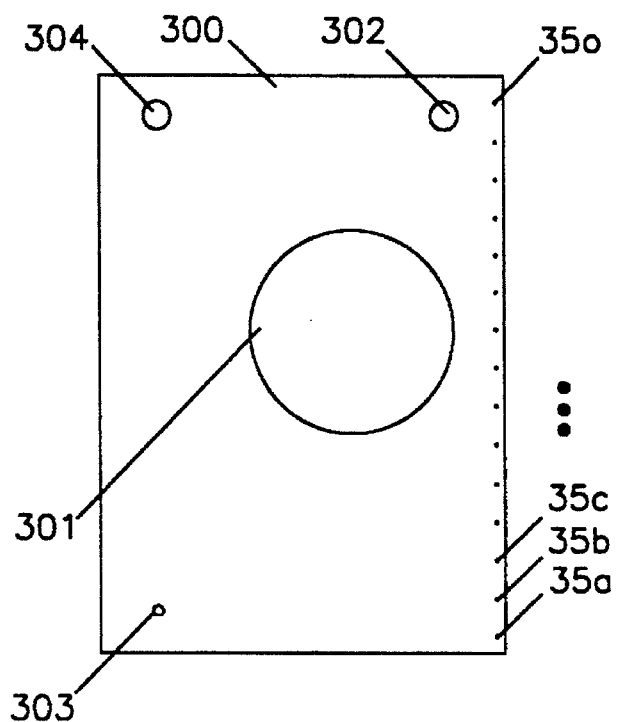
FIG. 13 is a drawing of the left panel in the isolation chamber of FIG. 10.

FIG. 13 shows left panel 300 in further detail. The large round opening 301 is used as a transfer port. The present invention uses an industry standard canister with two seals on the bottom (a double bottom canister), referred to as a beta can, which may be attached to a commercially available transfer port, referred to as, in one embodiment a 190 millimeter alpha port (190 mm hinged RTP Alpha door, nuclear type). This commercially available canister allows an operator of the sterile cell sorter to move items in and out of isolation chamber 90 without breaking the sterility of isolation chamber 90 once isolation chamber 90 has been sterilized. The items to be transferred into the isolation chamber (e.g. tubing and tools) are sterilized conventionally or obtained in a sterile form from available sources and then placed inside the sterilized canister in a sterile enclosure (e.g. conventional tissue culture laminar flow hood in a tissue room) and the canister is then sealed shut. While the canister is sealed shut, it is then attached to the alpha port which is secured to isolation chamber 90 around opening 301 with a compression seal (e.g. tightened by threads). Once the canister is attached and sealed to the alpha port, the canister can be opened, from the inside of isolation chamber 90 in order to remove the items in the canister into isolation chamber 90. The outside of the alpha port attaches and locks to the outside of the canister such that the two outside surfaces, which may not be sterile are sealed shut and do not contaminate (e.g. destroy sterility) the interior of the isolation chamber when the canister is opened from the inside of the isolation chamber 90. Naturally, the insides of the canister have been sterilized and the contents of the canister (e.g. tubing) are sterile and handled in a sterile enclosure so that, upon opening the canister from within the isolation chamber 90, the sterility of the isolation chamber 90 will not be destroyed. The canister and alpha port used in this embodiment are manufactured by La Calhene and may be obtained from Amsco Scientific; the canister is typically a 190 mm by 400 mm polyethylene container with a "beta" flange.

Note that without this transfer port, the only way solid physical objects can be moved in and out of isolation chamber 90 is by opening the door, thereby breaking the sterility of isolation chamber 90. Each time isolation chamber 90 is contaminated isolation chamber 90 must be sterilized again, which is a time-consuming (approximately 1–2 hours) process. Furthermore, breaking the sterility of isolation chamber 90 during the actual measuring and sorting of cells may contaminate or destroy an irreplaceable sample of cells. Therefore, the transfer port, which provides an alternative way to move items in and out of isolation chamber 90, is an extremely useful feature of the present invention.

The second opening 304 is used to insert a pressure sensor input (3/16 inch barb) into isolation chamber 90 for measuring the helium inputted into isolation chamber 90 during the leakage testing of isolation chamber 90. A 3/16 inch barb to 1/8 inch pipe bulkhead manufactured by Sunnyvale Valve is inserted into opening 304 and furthermore, is sealed to opening 304. A 1/8 inch pipe, which is attached to the bulkhead, is connected to a manometer (manufactured by Dwyer Corp.) used to display the air pressure inside isolation chamber 90.

The opening 302 is used by the sample input line to transport cells into the cell station for cell sorting. Sample input line 35a, shown in FIG. 3, is inserted into the isolation chamber through opening 302. The sample input line is a tube which is inserted into a hole passing through the center of the rubber boot having a slit. The slit is parallel to the hole running through the center of the rubber boot and is cut along the outer edge of the rubber boot through to the hole running through the center of the rubber boot. Once, the sample input line is properly inserted into the rubber boot, the rubber boot is then inserted into an Ultra-Torr fitting (model SS-12-UT-1-12 from Cajon), which is sealed to opening 302 with teflon tape. This particular Ultra-Torr fitting has an inside piece having a threaded surface and an outside piece which is screwed onto the inside piece. Furthermore, the inside piece and the outside piece are sealed by compression and an O-ring. The Ultra-Torr fitting with the inserted rubber boot and the teflon tape provides a leakproof connector allowing the sample input line to extend into isolation chamber 90 while maintaining the sterility of isolation chamber 90.

The last opening 303 in left panel 300 is used by the helium input line. A bulkhead manufactured by Genoa Corp., model number PMCD 10-02-12 (shut-off), is sealed to opening 303.

Furthermore, panel 300 also includes 15 small through holes 35a–35o, located along the right edge (when viewing the isolation chamber from the outside) of panel 300. These holes are used to attach the front door 600 to panel 300 with a hinge. In the embodiment where the chamber is secured to the table by angle brackets 561 and 562, panel 300 includes two further openings through which bolts are inserted to attach the chamber to the brackets.

Figure 14:
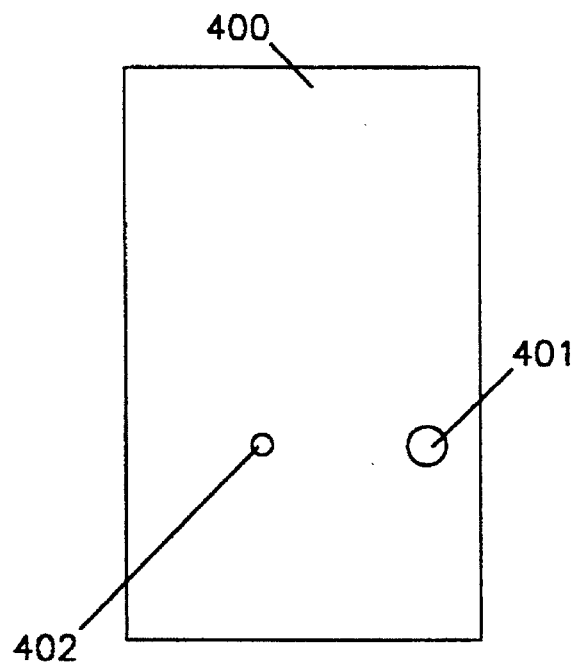
FIG. 14 is a drawing of the right panel in the isolation chamber of FIG. 10.

FIG. 14 shows a right panel 400 having two openings. The first opening 401, located along the primary laser optical path 45a shown in FIG. 4, is sealed shut with a piece of highly polished laser window BK-7 glass which is, in one embodiment 50 millimeters in diameter. This optical glass, manufactured by Melles Griot with a part number OZWBK005, is sealed to the inside of isolation chamber 90 around opening 401 with an O-Ring Grove around opening 401 and an O-Ring. Note that the laser window glass is optically transparent such that the primary laser beam travels through the glass without being significantly altered. In the embodiment where the chamber is secured to the table by angle brackets 561 and 562, panel 400 includes two further openings through which bolts are inserted to attach the chamber to the brackets.

The primary laser safety pipe, which extends from the primary laser source 45 (or a laser alignment assembly containing mirrors) along path 45a to illumination frame 43, is divided into two sections. The one section 45 c is located inside isolation chamber 42 and extends from the inside of isolation chamber 42 at opening 401 to a through opening in illumination frame 43 at location 43b, as shown in FIG. 4. The end of the primary laser safety pipe is inserted into the opening at 43b and thus is supported by illumination frame 43. The other section 45b of the primary laser safety pipe is located outside isolation chamber 42 and extends from isolation chamber 42 around opening 401, along path 45a, to the primary laser source (or to a laser alignment assembly). Attached to the outside of isolation chamber 90 around opening 401 is a half-round support 401a for the section 45b of the primary laser safety pipe (See FIGS. 9a and 10).

One advantage of having a primary laser safety pipe that is broken into two sections is that it is easier for the operator to align the primary laser beam path on the cells flowing in a microscopic jet of fluid through the measuring region (e.g. see the jet of FIG. 2, which may contain a stream of cells which stream is about 20 microns in diameter, and the cells may each be smaller than 20 microns). Once the section 45c of the primary laser safety pipe is in place and the isolation chamber has been sterilized, the operator needs only to adjust the section 45b of the primary laser safety pipe, which is located outside isolation chamber 90, in order to complete the alignment of the primary laser safety pipe. The primary laser safety pipe provides a protective shield around the primary laser beam thus making the environment around the cell sorter, both inside and outside isolation chamber 90, virtually safe from the primary laser beam.

The second opening 402 is used to insert the sheath fluid input line into isolation chamber 90. According to FIG. 3, the sheath fluid input line 37b is used to supply droplet generator 37 with sheath fluid from sheath fluid supply 33. The sheath fluid input line is inserted into a hole passing through the center of a rubber boot having a slit. The slit is parallel to the hole running through the center of the rubber boot and is cut along the outer edge of the rubber boot through to the hole running through the center of the rubber boot. Once, the sheath fluid input line is properly inserted into the rubber boot, the rubber boot is then inserted into an Ultra-Torr fitting (model SS-12-UT-1-12 from Cajon), which is sealed to opening 402 with teflon tape. This particular Ultra-Torr fitting has an inside piece having a threaded surface and an outside piece which is screwed onto the inside piece. Furthermore, the inside piece and the outside piece are sealed by compression and an O-Ring. The Ultra-Torr fitting with the inserted rubber boot and the teflon tape provides a leakproof connector allowing the sheath fluid line to extend into isolation chamber 90 while maintaining the sterility of isolation chamber 90.

Figure 15:
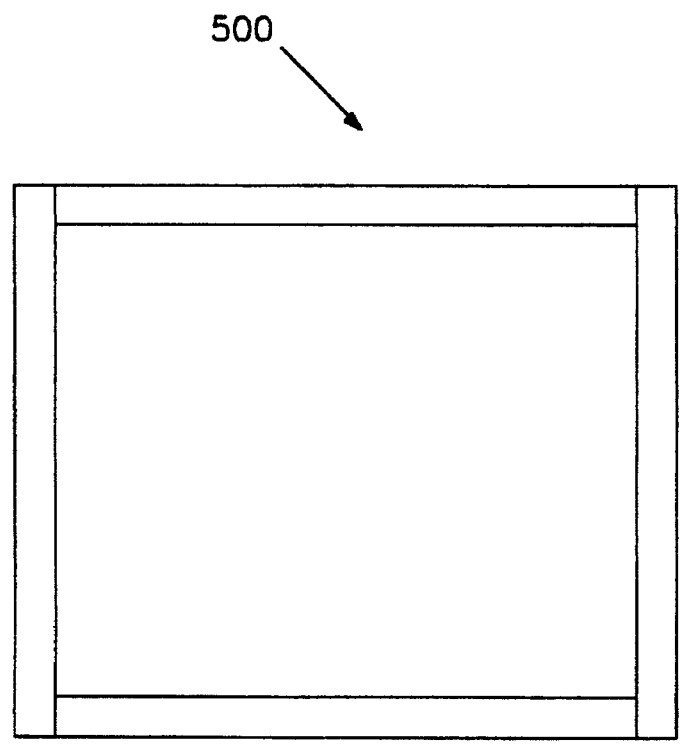
FIG. 15 is a drawing of the frame assembly in the isolation chamber of FIG. 10.
Figure 16:
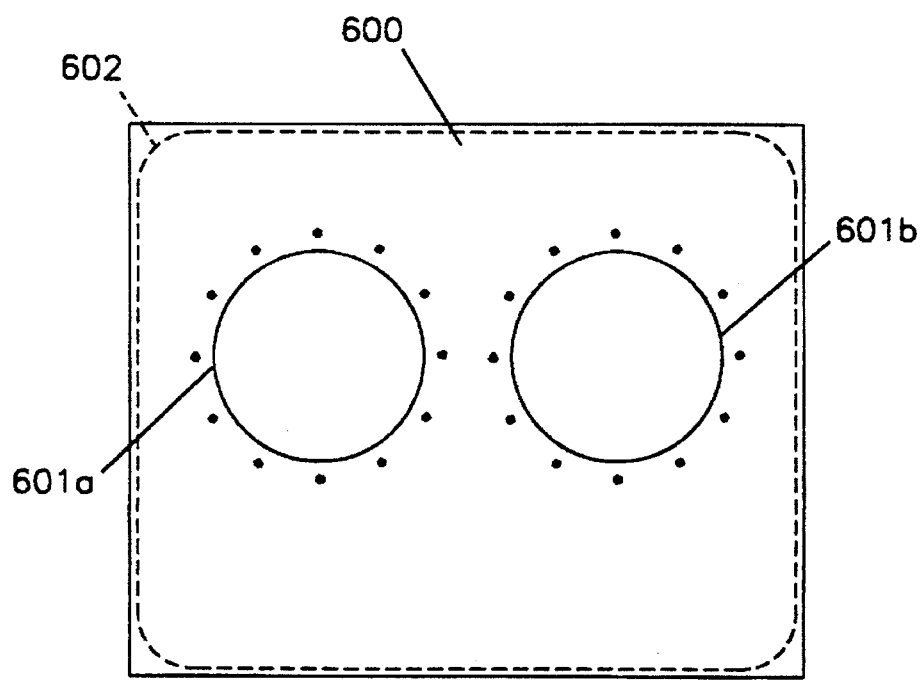
FIG. 16 is a drawing of the door and glove ports in the isolation chamber of FIG. 10.

The front panel includes a frame assembly 500, shown in FIG. 15, and a door 600, shown in FIG. 16, having glove ports 601a and 601b. The frame assembly 500 is sealed to door 600 by an O-Ring groove 602 around the perimeter of door 600 which groove is filled with closed foam. The closed foam used in this particular embodiment has a pressure sensitive adhesive (PSA) on one side thereby providing a seal when compressed against door 600.

Furthermore, along the left edge (when viewing the isolation chamber from the outside) of door 600 is 1 hinge with 15 screw holes that attach to corresponding holes 35a–35o along the right edge of left panel 300.

A cylindrical plastic glove sleeve is attached around the perimeter of each glove port 601a and 601b. In this embodiment, each cylindrical plastic glove sleeve has an O-Ring encapsulated at the end which is attached to a glove port (601a or 601b). The O-Ring provides a compression seal around the perimeter of glove port 601a and 601b when the O-Ring is bolted into a corresponding O-Ring groove on the isolation chamber 90 with two metal rings. The first metal ring is attached around each glove port from the outside of isolation chamber 90, and the second metal ring is attached around each glove port from the inside of isolation chamber. Compressed in between isolation chamber 90 and the second metal ring is the O-Ring in an O-Ring groove. Each cylindrical plastic glove sleeve has a disposable glove attached to the end extending inside the isolation chamber. The disposable gloves are also attached by an O-ring. It will be appreciated that numerous arrangements exist for these glove ports, the glove sleeves and the disposable gloves at the ends of the sleeves, due to the fact that these components and assembled arrangements of these components are commercially available.

Figure 17:
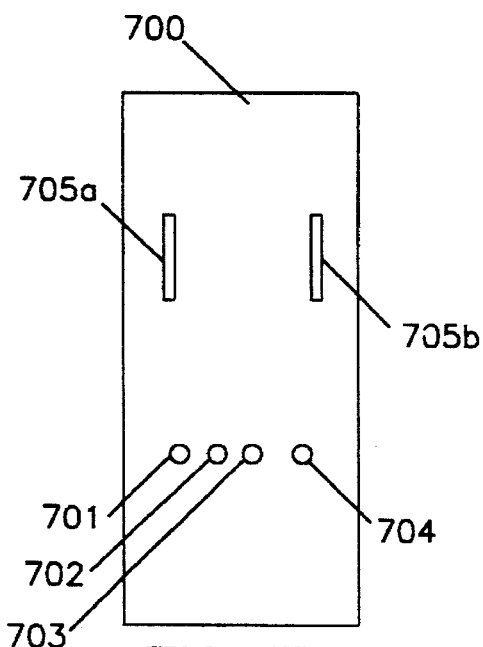
FIG. 17 is a drawing of a back panel in the isolation chamber of FIG. 10.

Panel 700 is a back panel having four openings, 701, 702, 703 and 704, as shown in FIG. 17. Opening 701 is used for the power input line for a camera located inside isolation chamber 90. Inside isolation chamber 90 is a first section of the power input line which is connected to the camera at one end and connected to a 2-pin Conxall 72822SG300 connector at the other end. The Conxall connector is sealed to opening 701 such that the camera can be powered on by a power supply external to isolation chamber 90 while maintaining the sterility of isolation chamber 90. A second section of the power input line is connected to the Conxall connector from the outside at one end and to a power supply at the other end.

Opening 704 is used for camera video output and is connected to opening 704 by an Amphenol 31-220G-RFX bulkhead. The bulkhead is sealed around opening 704 by compression (e.g. washers and threads in the bulkhead) such that a first section of the camera video output line can be connected to the bulkhead from the inside of the isolation chamber and a second section of the camera video output line can be connected to the bulkhead from the outside of the isolation chamber.

Opening 702 is for a sealed electrical connector for providing power to a droplet delay indicator.

Opening 703 is used by the forward scattering light detector. The forward scattering light is detected by a photo diode located inside isolation chamber 90. The photo diode is connected to a wire which is connected to a bulkhead connector (Amphenol 31-220G-RFX) sealed to opening 703. A second wire on the outside of isolation chamber 90 is connected the bulkhead connector such that the forward scattering light can be converted into electrical signals outside the isolation chamber.

Attached to the inside of panel 700 are camera brackets 705a and 705b. These brackets are used to store the camera inside isolation chamber 90 when the camera is not being used. It will be appreciated that this camera may be used with a strobed illumination source to view the jet and droplets from the droplet generator.

Figure 18:
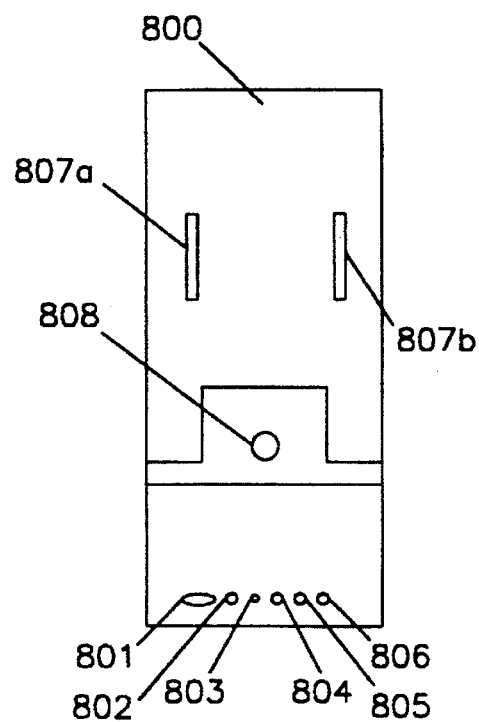
FIG. 18 is a drawing of a second back panel in the isolation chamber of FIG. 10.

Panel 800, shown in FIG. 18, is another back panel. Opening 801 is used to insert high voltage input cables into isolation chamber 90 through an Alden D300UB14 connector. The high voltage input cables supply the defection plates (e.g. deflecting system 26 shown in FIG. 2) with power. The Alden connector is sealed around opening 801 with silicone.

A 4 pin Conxall 7282-4SG300 connector used for the laser safety interlock is sealed to opening 802. The safety interlock uses a glass filter (a BK-7 optical window) that fits into the front of the separation chamber, which is the chamber that encloses the measuring region inside the illumination frame. This safety device ensures operator safety when using the laser beams. When inserted properly (e.g. the filter is present and is fully in place), this filter actuates conventional solenoid shutters to open the primary and secondary lasers. This particular embodiment uses a conventional non-contact switch to sense whether the filter is fully in place. A line connects the laser safety interlock to the Conxall connector from the inside of isolation chamber 90 and a second line connects the Conxall connector from the outside of isolation chamber 90 to conventional shutters on the primary and secondary laser sources.

Opening 803 uses a Swagelock SS-400-11-2 connector to insert the vacuum tube inside isolation chamber 90. The connector is sealed around opening 803. Debris that may clog up the droplet generator is removed through this tube and is discarded outside isolation chamber 90.

Openings 804, 805 and 806 use an Amphenol 31-220G-RFX bulkhead connector. Opening 804 is used for the strobe driver input, opening 805 is used for the droplet charge input, and opening 806 is used for the crystal drive input. The strobe driver is used to strobe the sort stream in order to view a still image of the stream on the camera monitor. The crystal driver input is used to power the ultrasonic transducer (e.g. 23b in FIG. 2) to vibrate the nozzle to form uniform droplets at a certain interval. The droplet charge input is used to provide the power/charge which is used to selectively charge droplets after leaving the nozzle of the droplet generator.

Utility brackets 807a and 807b are used to support a utility basket 93 or some other storage unit inside isolation chamber 90. The utility basket 93, shown in FIG. 9b, provides a storage area within isolation chamber 90 for tools and equipment when not being used. The tools may be inserted into the chamber 90 by opening the door on the front of the chamber and then the tools and chamber may be sterilized. In one embodiment, the utility basket is made out of a metal mesh material (see FIG. 9b). The mesh utility basket ensures that the surface area of its contents are exposed to the hydrogen peroxide vapor during the sterilization process thereby properly sterilizing the contents being stored by the utility basket. The basket may alternatively be constructed out of a plastic mesh material.

The microscopic objective lens (e.g. lens 47 shown in FIG. 4), surrounded by a stainless steel tubing which is a part of the detector table (e.g. table 44), is also inserted through panel 800 by using opening 808. After inserting the stainless steel tubing into opening 808, the detector table is pushed near panel 800. In this particular embodiment, a ⅛ inch closed cell foam gasket (PSA) in the shape of a circular ring (inside diameter 25.4 mm and outside diameter 50 mm) is placed in between the detector table and panel 800 around the stainless steel tubing. By using the closed cell foam, a compression seal is formed around opening 808 while maintaining some flexibility in this seal. The flexibility of this seal between this tubing and the opening 808 ensures that there is, to some extent, mechanical isolation from the isolation chamber for the microscope objective lens and the other optics on the detector table. The mechanical isolation is achieved by the flexibility of the seal, which acts as a shock absorber, as is the case with the mechanical isolation described above between the illumination frame and the isolation chamber.

Figure 19:
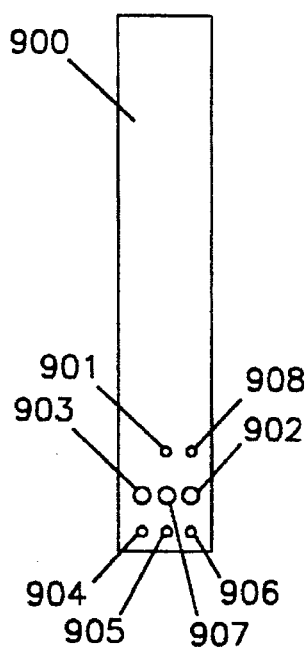
FIG. 19 is a drawing of a third back panel in the isolation chamber of FIG. 10.

FIG. 19 shows a third back panel 900. Opening 901 is used by the sample pressure input line 35b, shown in FIG. 3. According to FIG. 3, the sample pressure input line 35b is used to supply cell station 35 with air pressure. This air pressure line inside the isolation chamber and outside the isolation chamber is connected by a SSA7470 connector manufactured by S4J company and is also sealed to opening 901.

Sealed to opening 902 is a Conxall 7282-5SG300 (5 pin) connector. A conventional magnetic stirrer base, used to stir a magnetic stirrer (e.g. stirrer 84 shown in FIG. 8), is powered by a line that is connected to this Conxall connector.

Opening 903 is used by an illuminator which provides light for the cells flowing in the stream of fluid in the measuring region of the illumination frame. A Conxall 7282-4SG300 (or 7282-2SG300) connector, which is sealed around opening 902 is used to connect the tubing from the illuminator through the walls of the isolation chamber.

The cooling line in 38a and cooling line out 38b, shown in FIG. 3, pass through openings 905 and 904. Each cooling line uses two PLCD 160-04-12 connectors made by CPC Inc.

Waste from the cell collector is channeled through a line (e.g. line 34b shown in FIG. 3) which passes through opening 906 to be discarded outside isolation chamber 90 by the vacuum system. This waste outlet line 34b, shown in FIG. 3, uses a S4J company connector model number SSA7470.

Opening 907 in panel 900 is used by the control wires which control the pinch valve solenoids. A pinch valve may be used to stop the flow in the sheath fluid line, the sample input line, or the vacuum tubes.

Opening 908 may be used to provide an exit port for a tube carrying waste away, e.g. waste line 34a shown in FIG. 3.

Figure 20:
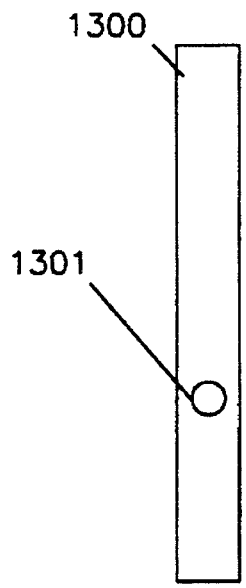
FIG. 20 is a drawing of a second right panel in the isolation chamber of FIG. 10.

The last panel in isolation chamber 90 to be described in detail is the right panel 1300, as shown in FIG. 20. Opening 1301 has the same type of seal as opening 401 in FIG. 14 which is used to provide a transparent optical laser window for the secondary laser source. The secondary laser safety pipe is divided into two sections 46b and 46c (shown in FIG. 4), similar to the primary laser safety pipe, and is supported in the same manner as the primary laser safety pipe. According to FIG. 4, the secondary laser beam travels along path 46a which is 20 degrees counter clockwise from the primary laser path 45. Also, 20 degrees counter clockwise from right panel 400 is right panel 1300. In this embodiment, the end of the internal section of the secondary laser safety pipe is supported by illumination frame 43 by inserting this section of secondary laser safety pipe into a hole in illumination frame 43, located at point 43c.

Though the present invention has been described by referring to several specific embodiments, numerous alternative embodiments of the present invention exist within the scope of the present invention. While the present invention provides a sterile cell sorting apparatus and a method for sterilizing and using the apparatus, it will be appreciated that sterile cell sorting provides many further uses in accordance with the present invention. For example, it has been found that separation of one subpopulation of cells that is very rare (e.g. pluripotent hematopoietic stem cells) from several other subpopulations of cells (e.g. other hematopoetic cells) in a sample of cells is possible. Where such a rare subpopulation is capable of multiplying and developing into several other (more developed) subpopulations of cells, the separated rare subpopulation may be used to regenerate (e.g. in vivo) the other subpopulations. Moreover, in the case where the other subpopulations of cells contain, for example, virally infected cells or malignant cells, it has been found possible to isolate/separate the rare subpopulation of cells which are not similarly infected or malignant. In general, the sterile cell sorting separation may be used to separate normal cells from aberrant cells to the extent these aberrant cells can be distinguished from the normal cells. Often then, the isolated normal cells (e.g. pluripotent hematopoetic stem cells) which have been maintained in a sterile environment may be injected or otherwise administered to a patient for treatment of the patient. Moreover, various procedures may be applied to such isolated cells after a sterile cell sorting operation in order to prepare the sorted cells for a treatment of a patient before administering the sorted cells to the patient. These procedures include culturing the cells, genetically modifying the cells and/or incorporating drug delivery systems into the cells.

The present invention may also be used with alternative embodiments of cell sorters. For example, cell sorters which use an arc lamp or several arc lamps as the light source or sources may be used with the present invention. There are numerous examples of such arc lamp sources being used with cell sorters. Also cell sorters which use closed chamber measuring may be employed with the present invention; in this case, the measuring region is within a glass (or other transparent) container (typically a rectangular cross-sectionally shaped glass container for the laminar flow of the combination of sheath fluid and sample cell stream) rather than being in a jet in open air (as shown in FIG. 2). Other alternative embodiments may use the well known technique of electrical (Coulter) impedance measurement to perform a flow cytometry operation before sorting the cells. Furthermore, the apparatus and method of the invention may be used with a high speed cell sorter. An example of a high speed sorter used to sort viable cells which may be used with the present invention is described in published PCT application US 93/08205.

We claim:

1. A sterile cell cytometric system for measuring at least one property of a sample of cells, said sterile cell cytometric system comprising:
   a supporting surface;
   an isolation chamber providing an enclosed environment which can be sterilized;
   an illumination frame located within said isolation chamber wherein said illumination frame is fixedly attached relative to said supporting surface, said illumination frame supporting a measuring region wherein said at least one property of said sample of cells is measured, wherein said illumination frame is mechanically isolated from said isolation chamber.

2. The sterile system as in claim 1 wherein said illumination frame further comprises a plurality of standoffs inserted through openings in said isolation chamber wherein said plurality of standoffs support said illumination frame, said illumination frame and said isolation chamber being sealed in said openings by a flexible sealant and wherein said at least one property is measured in order to selectively remove certain cells from said sample of cells depending on a measurement of said at least one property.

3. The sterile system as in claim 1 wherein said isolation chamber has a first section and a second section wherein said first section is positioned in front of said second section, said second section is bolted to said supporting surface wherein said supporting surface provides support for said isolation chamber, said first section extends beyond said supporting surface such that said first section overhangs said supporting surface.

4. The sterile system as in claim 1 further comprising a detector table wherein said detector table is supported by said supporting surface, said detector table includes optics for collecting light wherein said optics is located outside said isolation chamber, said detector table further includes an objective lens wherein a portion of said objective lens extends inside said isolation chamber, said portion of said objective lens extending inside said isolation chamber being inserted into a through hole in said illumination frame in order to collect light emitted by said sample of cells.

5. The sterile system as in claim 1 further comprising a light source wherein said light source is supported by said supporting surface, said light source includes at least one light beam source and a corresponding light beam safety pipe wherein said corresponding light beam safety pipe extends inside said isolation chamber and is inserted into a through hole in said illumination chamber thereby providing said illumination frame with at least one beam of light for measurement of said at least one property of said sample of cells.

6. The sterile system as in claim 1 further comprising a sterilization system, said sterilization system is located outside said isolation chamber, said sterilization system sterilizing an area located within said isolation chamber.

7. The sterile system as in claim 1 further comprising a sterilization system, wherein said sterilization system injects a sterilant into said isolation chamber to sterilize an area located within said isolation chamber by increasing a concentration of said sterilant within said isolation chamber to an effective level, further wherein said sterilization system further recirculates filtered air in said isolation chamber to ventilate said area located within said isolation chamber by reducing said concentration of said sterilant to a negligible level.

8. The sterile system as in claim 1 wherein said isolation chamber includes a panel having at least one glove port having a glove wherein an operator located outside said sterile system may handle objects within said isolation chamber without contaminating said sterile system.

9. The sterile system as in claim 1, wherein said isolation chamber includes a transfer port having a first and a second part linked by a locking mechanism wherein said second part is a canister and wherein objects located outside said isolation chamber may be placed inside said second part and then placed inside said isolation chamber without breaking sterility.

10. The sterile system as in claim 1, wherein said isolation chamber includes a portion of a wall of said isolation chamber and wherein a first laser safety pipe and a second laser safety pipe are optically coupled to said isolation chamber at said portion.

11. The sterile system as in claim 1, wherein said isolation chamber includes a source of pressurized dry gas for drying spills within said isolation chamber.

12. The sterile system as in claim 1, wherein said isolation chamber includes a mesh basket for storing items within said isolation chamber.

13. The sterile system as in claim 11 wherein said isolation chamber includes a first wall and a second wall and wherein a light source provides a first light beam and a second light beam, said first light beam and said second light beam having a first angle between said light beams, said first light beam being directed through said first wall and said second light beam being directed through said second wall, and wherein said first wall and said second wall having a second angle between said walls which substantially equals said first angle.

14. The sterile system as in claim 1 wherein said cells are pluripotent hematopoietic stem cells.

15. The sterile system as in claim 1 wherein said illumination frame supports a droplet generator and wherein said droplet generator is coupled to a cell station which supplies said sample of cells to said droplet generator, wherein said cell station is pressurized with a gas to drive said sample of cells from said cell station to said droplet generator.

16. The sterile system as in claim 15 wherein said isolation chamber includes a seal at a wall of said isolation chamber and wherein a first laser safety pipe and a second laser safety pipe are optically coupled to said isolation chamber at said seal.

17. The sterile system as in claim 1 further comprising electrically controlled valves for controlling flow of fluids and gas pressure in tubes, said tubes being located in said isolation chamber.

18. The sterile system as in claim 12 wherein said valves are pinch valves and wherein sample tubes comprise a tube of delivering said sample of cells.

* * * * *